(12) United States Patent
Dormer et al.

(10) Patent No.: US 8,740,872 B2
(45) Date of Patent: Jun. 3, 2014

(54) MAGNETICALLY-TARGETED TREATMENT FOR CARDIAC DISORDERS

(75) Inventors: Kenneth J. Dormer, Edmond, OK (US); Sunny S. Po, Edmond, OK (US); Benjamin J. Scherlag, Oklahoma City, OK (US); Carey N. Pope, Stillwater, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 465 days.

(21) Appl. No.: 12/907,806

(22) Filed: Oct. 19, 2010

(65) Prior Publication Data

US 2012/0095442 A1 Apr. 19, 2012

(51) Int. Cl.
*A61M 31/00* (2006.01)

(52) U.S. Cl.
USPC ........... 604/507; 424/9.3; 424/9.34; 424/9.36

(58) Field of Classification Search
USPC .......................... 604/507; 424/9.3, 9.34, 9.36
See application file for complete search history.

(56) References Cited

U.S. PATENT DOCUMENTS

| | | | |
|---|---|---|---|
| 5,427,767 A | 6/1995 | Kresse et al. | |
| 5,705,195 A | 1/1998 | Volkonsky et al. | |
| 6,048,515 A | 4/2000 | Kresse et al. | |
| 6,200,547 B1 | 3/2001 | Volkonsky et al. | |
| 6,514,481 B1 | 2/2003 | Prasad et al. | |
| 6,743,779 B1* | 6/2004 | Unger et al. | 514/44 R |
| 6,977,080 B1* | 12/2005 | Donovan | 424/247.1 |
| 7,485,624 B2 | 2/2009 | Donovan | |
| 7,709,440 B2 | 5/2010 | Shaari | |
| 7,723,311 B2 | 5/2010 | Seeney et al. | |
| 7,731,977 B2 | 6/2010 | Ackerman | |
| 2005/0175703 A1* | 8/2005 | Hunter et al. | 424/486 |
| 2006/0002852 A1 | 1/2006 | Saltzman et al. | |
| 2006/0025713 A1* | 2/2006 | Rosengart et al. | 604/5.02 |
| 2006/0057211 A1* | 3/2006 | Chorny et al. | 424/486 |
| 2006/0228421 A1 | 10/2006 | Seeney et al. | |
| 2007/0196281 A1 | 8/2007 | Jin et al. | |
| 2008/0241262 A1 | 10/2008 | Lee et al. | |
| 2009/0216320 A1 | 8/2009 | Levy et al. | |
| 2009/0226521 A1 | 9/2009 | Smyth et al. | |
| 2009/0287036 A1 | 11/2009 | Shapiro et al. | |
| 2010/0036480 A1 | 2/2010 | Viller et al. | |
| 2010/0079142 A1 | 4/2010 | Fontius | |
| 2010/0204674 A1 | 8/2010 | Forbes et al. | |

OTHER PUBLICATIONS

Forbes et al., "An Approach to Targeted Drug Delivery Based on uniform Magnetic Fields." IEE Transactions on Magnetics, vol. 39, No. 5, Sep. 2003.

(Continued)

*Primary Examiner* — Kevin C Sirmons
*Assistant Examiner* — Edelmira Bosques
(74) *Attorney, Agent, or Firm* — Dunlap Codding, P.C.

(57) ABSTRACT

The present disclosure describes a method for targeted delivery of permanently-acting or temporarily-acting neurotoxins, neurosuppressants, or other compounds having a neurologic effect to specific locations of the heart, including for example, but not limited to, nodes of the cardiac autonomic nervous system such as the atrial ganglionated plexi (GP). Chemical ablation of the atrial GP as described herein via magnetically-targeted magnetically-susceptible nanoparticles can effectively suppress GP activity and atrial fibrillation related, thereto without permanent damage to either myocardium or intrinsic CANS.

25 Claims, 7 Drawing Sheets
(1 of 7 Drawing Sheet(s) Filed in Color)

(56) References Cited

OTHER PUBLICATIONS

Douziech-Eyrolles et al., "Nanovectors for anticancer agents based on superparamagnetic iron oxide nanaparticles." International Journal of Nanomedicine: 2 (4), pp. 541-550, (2007).

Hou et al., "Ganglionated Plexi Modulate Extrinsic Cardiac Autonomic Nerve Input." Journal of the American College of Cardiology by the American College of Cardiology Foundation, Elsevier Inc., vol. 50, No. 1, (2007).

Forbes et al., "Validation of High Gradient Magnetic Field Based Drug Delivery to Magnetizable Implants Under Flow." IEEE Transactions on Biomedical Engineering, vol. 55, No. 2, Feb. 2008.

Avilès et al., "Isolated swine heart ventricle perfusion model for implant assisted-magnetic drug targeting." International Journal of Pharmaceutics 361, pp. 202-208, Elsevier B.V., (2008).

Basak et al., "Transport characteristics of nanoparticle-based ferrofluids in a gel model of the brain." International Journal of Nanomedicine, Dover Medical Press Ltd., vol. 4, pp. 9-26, (2009).

Polyak et al., "Magnetic targeting for site-specific drug delivery: applications and clinical potential." Informa Healthcare, London, vol. 6, pp. 53-70, Issued Jan. 2009.

Kumar et al., "Multifunctional magnetic nanoparticles for targeted delivery." Nanomedicine: NBM, vol. 6, pp. 64-69, doi:10.1016/j, (2010).

Hoare et al., "A Magnetically Triggered Composite Membrane for On-Demand Drug Delivery." American Chemical Society, Nano Letters, vol. 9, No. 10, pp. 3651-3657, (2009).

Chorny et al., "Targeting stents with local delivery of paclitaxel-loaded magnetic nanoparticles using uniform fields." PNAS, vol. 107, No. 18, pp. 8346-8351, May 2010.

Yu et al., "Autonomic Denervation Using Magnetic Nanoparticles." Heart Rhythm Society, Heart Rhythm Journal, vol. 7, Issue 5S, PO1-13, May 2010.

Petros et al., "Strategies in the design of nanoparticles for therapeutic applications." Macmillan Publishers Limited, Nature Reviews, Drug Discovery, vol. 9, pp. 615-627, Aug. 2010.

* cited by examiner

MAGNETICALLY-TARGETED TREATMENT FOR CARDIAC DISORDERS

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND

The presently disclosed and claimed inventive concepts relate to targeted therapeutic delivery systems and methods to treat cardiac disorders, in particular cardiac arrhythmias, and more particularly, but not by way of limitation, atrial fibrillations such as drug-refractory atrial fibrillation.

Atrial fibrillation (AF) is the most common cardiac arrhythmia requiring treatment and frequently progresses from paroxysmal AF to permanent AF and accounts for nearly 20% of the strokes in the U.S. AF inflicted approximately 2.3 million Americans in 2004[1,2] and cost the health care system nearly $12 billion a year to treat AF and AF-related strokes.[2] By the year 2050, the number of AF patients is projected to increase to 16 million as the population ages.[3] Nearly half of AF patients are refactory (i.e., do not respond) to anti-arrhythmic drugs and require non-pharmacologic treatment, i.e., surgical or catheter ablation. Clinical trials aimed at a pharmacological treatment of AF resulted in a 50% success rate after one year follow-up. The other 50% have been shown to have drug and cardioversion resistance. These patients are now treated with costly and time consuming catheter based application of radiofrequency (RF) energy within the heart to isolate the focal firing sites in the pulmonary vein (PV) myocardial sleeves from the rest of the atria. Currently, there is only one RF ablation catheter approved by FDA for atrial ablation procedures. Off-label use of all other surgical ablation devices had raised significant regulatory concerns and litigations.[4] Standard catheter or surgical ablation procedures produce lesion sets to isolate the pulmonary vein (PV)-atrial junction, containing the presumed triggers and/or substrate for AF.[5-8] However, in a single procedure, PV antrum isolation only leads to approximately 60⁺-70⁺% success for the earliest stage of AF (paroxysmal AF) and less than 50% for more persistent forms of AF.[5-8] This approach, widely practiced worldwide, has many drawbacks including relatively low success rate (~70%) and various complications, including PV stenosis, cardiac tamponade, esophageal injury and minor or major strokes. Despite all the advances in ablation technologies in the past 6 years, success of AF ablation has not improved. The unsatisfactory efficacy of AF ablation is mainly due to insufficient understanding of the electrophysiological mechanism(s) underlying the initiation of AF and its progression into more persistent forms of AF. A mechanistically-based therapy is still lacking.

Prior studies of AF initiation in patients and animals indicate that (unbalanced) activation of both sympathetic and parasympathetic nervous systems often precede AF onset.[9-14] Mammalian hearts are dually innervated by the extrinsic and intrinsic cardiac autonomic nervous system (CANS). It is known that the intrinsic CANS is a neural network composed of many ganglionated plexi and interconnecting nerves and/or neurons.[15-19] In this neural network, bilateral autonomic inputs come together at many "integration centers" before giving rise to final common pathways that control cardiac rhythm and force of contraction.[15,16,18,19] These intrinsic integration centers are located in the ganglionated plexi (GP) which are overlain by epicardial fat pads. In mammalian hearts, four major atrial GP (anterior right GP, ARGP; inferior right GP, IRGP; superior left GP, SLGP; and inferior left GP, ILGP) are located adjacent to the junction of the atrium and four pulmonary veins.[14-17] In previous studies, we have shown that electrical stimulation or injection of acetylcholine into the GP near the PV-atrial junction can initiate sustained AF arising from the PV-atrial junction.[13,14,19] Ablation of the four major atrial GP and ligament of Marshall markedly suppress the inducibility and maintenance of AF in multiple animal models, including the rapid atrial pacing model.[20,21] Notably, the lesion sets of a standard AF ablation (PV antrum isolation) involve ablation of two or three of the four major atrial GP, the ligament of Marshall and numerous autonomic nerves, indicating that autonomic denervation is a major contributor to the antiarrhythmic effects of AF ablation. Importantly, ablations involving only the major atrial GP, without PV antrum isolation, yielded similar results to the standard PV antrum isolation but produced significantly less collateral damage to the atrial myocardium and possible less iatrogenic left atrial flutter.[22-24] While re-innervation may occur 1-6 month after RF catheter ablation procedures[25-27], the clinical benefits of GP ablation lasted 16-18 months,[22-24] suggesting that permanent injury to the intrinsic CANS, particularly the autonomic neurons, may not be necessary to inhibit AF.

Targeted drug delivery is an increasingly used nanomedicine technology in which delivery of therapeutics to target tissues may increase drug efficacy, eliminate side effect and reduce costs. Polymeric nanoparticles whose diameters range from 10-300 nanometers[28-36] can be formulated as nanocomposites with encapsulated drugs for burst and/or controlled release.[31-33] Superparamagnetic nanoparticles, approved in the early 1990s for clinical magnetic resonance imaging enhancement, can be encapsulated in polymers or silicon and pulled into tissues to produce more precise lesion sets and thereby reducing collateral damages.

Standard AF ablation requires the creation of two circumferential lesions to isolate the antrum of all the PVs. Currently, atrial ablation strategies focus on isolating and/or destroying atrial tissue that presumably is responsible for AF, although the long-term consequences of extensive damage to the atrial myocardium, neural elements and atrial contractility are yet to be discovered.

Multiple basic science studies have demonstrated significant impact on AF after the major left atrial GPs were ablated. Using a rapid atrial pacing model, Lu et al showed that shortening of the effective refractory period (ERP), increase of ERP dispersion as well as increased AF inducibility caused by rapid atrial pacing for 3 hours were all reversed by ablation of the 4 major atrial GP and ligament of Marshall (LOM).[48] In animals receiving GP ablation first, rapid atrial pacing for 6 hours failed to change the ERP, ERP dispersion and AF inducibility. The authors proposed that autonomic denervation may serve as a therapeutic modality to prevent paroxysmal AF to progress to more persistent forms of AF. Other animal studies also demonstrated that after ablation of the GP and LOM, AF became more difficult to initiate and sustain; normalization of the fractionated potentials often led to the termination of AF after GP ablation.[62,63] Moreover, GP ablation may also convert AF from the focal form of AF to the macro-reentrant form of AF, which was more responsive to antiarrhythmic drugs.[63]

Several clinical studies have indicated the benefits of autonomic denervation by targeting the major atrial GPs identified by high frequency stimulation. When GP ablation was combined with PV isolation, the success rate improved.[37-39] Addition of PV isolation produced a long-term success rate higher than 90% in patients with paroxysmal AF.[37,39] A series of recent manuscripts by Pokushalov et al also reported similar success rate in AF ablation targeting only the major atrial GPs in comparison to the standard PV isolation approach.[40-42]

As noted, clinical studies demonstrated that GP ablation as an adjunct therapy to PV isolation improved the outcome of AF ablation whereas GP ablation alone produced a success rate similar to the standard PV isolation[37-42]. This denervation-only ablation strategy has the advantage of producing more focused lesion sets and potentially carrying a smaller risk of producing iatrogenic macro-reentrant left atrial tachycardia.

A method of direct (targeted) treatment of cardiac tissues for the inhibition of AF and other cardiac disorders with less extensive injury to cardiac tissues and which is non-permanent would be highly desirable.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

DETAILED DESCRIPTION

Figure 1:
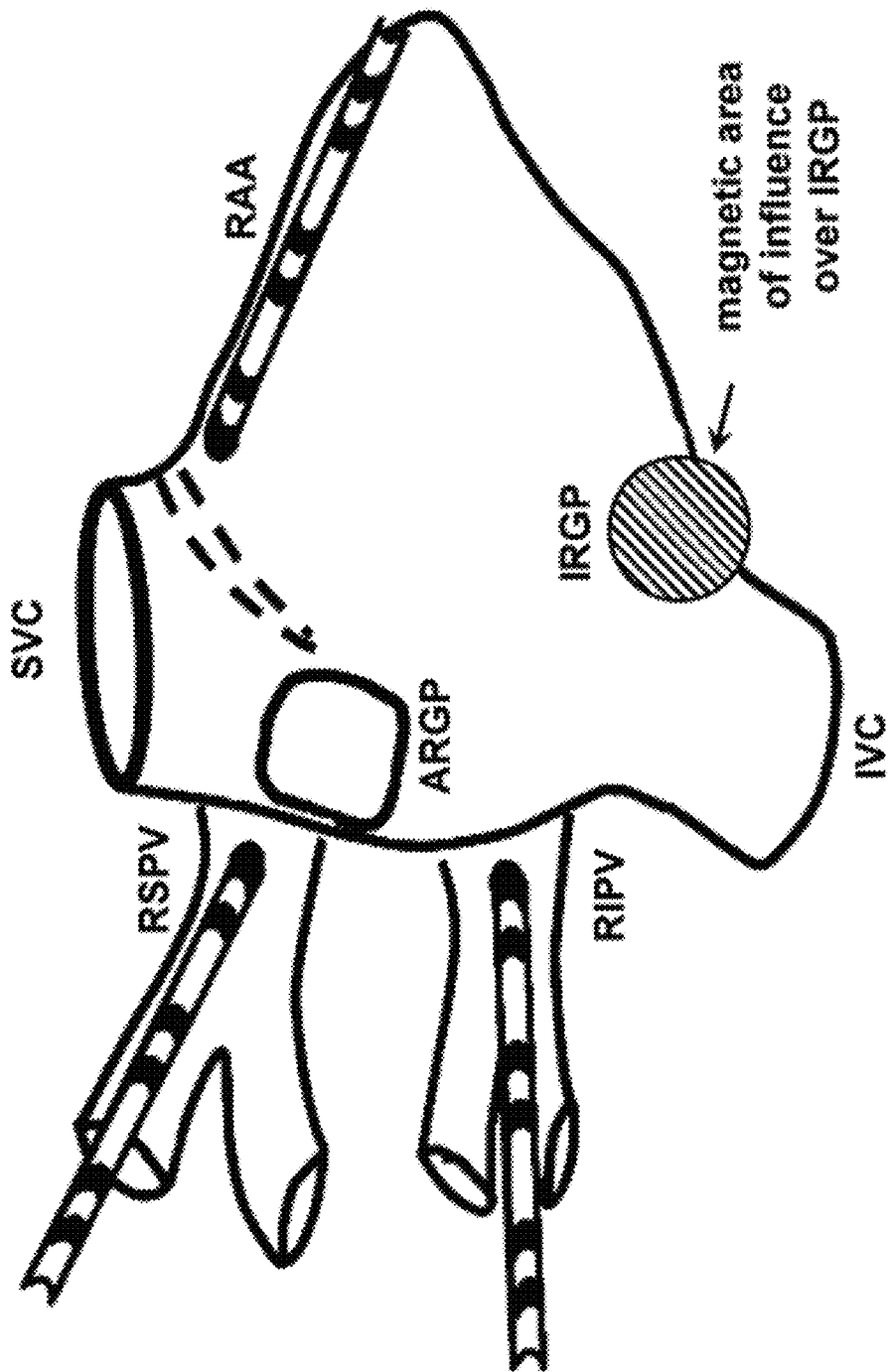
FIG. 1 is a diagrammatic representation of the atria as seen from a right sided thoracotomy. Electrode catheters were sutured at the right superior pulmonary vein (RSPV) and right inferior pulmonary vein (RIPV) and on the right atrial appendage (RAA). An example magnetic area (volume) of influence is shown for the IRGP. Abbreviations: SVC=superior vena cava; ARGP and IRGP: anterior right and inferior right ganglionated plexi, respectively; IVC=inferior vena cava.

Targeted drug delivery is an emerging technology in which therapeutic delivery to tissues can increase drug efficacy, alleviate side effects and reduce costs. Polymeric nanoparticles can be formulated with absorbed, attached, embedded, or encapsulated drugs for burst and/or controlled release.[43-47] In the presently disclosed and claimed inventive concepts, magnetically targeted drug delivery is used to treat various cardiac disorders, such as arrhythmias.

Atrial fibrillation, for example, is the most commonly encountered cardiac arrhythmia and affects 2.5 million people in the United States alone. As the population ages, the incidence is projected to increase to 6 million in year 2029, a significant portion of whom will have drug-refractory AF and require ablation.[70] Catheter or surgical ablation carries significant risks of serious complications and is very costly. Targeted drug delivery as described in the present disclosure provides a less invasive and less expensive therapeutic modality. With the advances in stereotactic localization by externally applied magnetic field, it is possible to selectively deliver the MNPs to one or more GPs to achieve autonomic denervation and treat AF without the risks of serious complications associated with catheter or surgical ablation or the side effects from long-term anti-arrhythmic therapy.

The present disclosure describes a method for targeted delivery of permanently-acting or temporarily-acting neurotoxins, neurosuppressants, or other active agents having a neurologic or other physiologic or therapeutic effect to specific locations of the heart, including for example, but not limited to, the cardiac autonomic nervous system such as the atrial ganglionated plexi (GP). Chemical ablation of the atrial GP as described herein via magnetically-targeted magnetically-susceptible nanoparticles delivering active agent, can effectively suppress GP activity and atrial fibrillation related, thereto without permanent damage to either myocardium or intrinsic CANS.

As used herein, the words “comprising” (and any form of comprising, such as “comprise” and “comprises”), “having” (and any form of having, such as “have” and “has”), “including” (and any form of including, such as “includes” and “include”) or “containing” (and any form of containing, such as "contains" and "contain") are inclusive or open-ended and do not exclude additional, unrecited elements or method steps.

The term "or combinations thereof" as used herein refers to all permutations and combinations of the listed items preceding the term or similar terms in the specification.

The use of the word "a" or "an" when used alone, or in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." The term "plurality" refers to "two or more." Throughout this application, the term "about" is used to indicate that a value includes the inherent variation of error for the device, the method being employed to determine the value, or the variation that exists among the study subjects.

Where used herein the term "subject" refers to animals having a CANS, particularly mammals, and more particularly to humans, primates, apes, dogs, cats, horses, lab animals, livestock animals, and zoo animals.

In one embodiment, the presently disclosed and claimed inventive concepts are for the purpose of preventing or reducing atrial arrhythmias in patients, especially atrial fibrillation. The presently disclosed and claimed inventive concepts are methods for applying magnetically-susceptible nanoparticles, via the vascular system, and targeting them to one or more of the four ganglionated plexi and/or the ligament of Marshall on the epicardial surface of the heart and being able to release the therapeutic chemical ("active agent" or "bioactive agent") for causing selective temporary or permanent neuropathy. Additionally, the embolization of the MNPs may also cause ischemia and subsequent selective temporary or permanent neuropathy of autonomic neurons in the GP. Additionally, the alternating electromagnetic oscillation of the MNPs optionally will allow for controlled warming therefore, controlled release of the bioactive agent by elevating the temperature of the MNPs thereby causing swelling or contraction of the polymer shell of the MNPs.

Millions of patients have atrial arrhythmias who have few or no alternatives to cure the atrial fibrillation. The methods of the presently disclosed and claimed inventive concepts employ, to various degrees, nanotechnology, magnetic targeting, cardiac catheterization, a nanocomposite drug (bioactive agent) delivery system, temperature-controlled release of the bioactive agent and microvascular embolization, all for the purpose of selectively reducing the (autonomic) activity emanating from (intrinsic autonomic) GP, which in combination with the extrinsic autonomic innervation of the heart is responsible for cardiac arrhythmias, especially those of the atria.

As described elsewhere herein, the MNPs used in the presently disclosed and claimed inventive concepts comprise a biocompatible polymeric outer coating (shell) which contains a magnetically-susceptible inner core (e.g., iron oxides) and which also contains and transports the active agent (drug, therapeutic, bioactive compound or agent, or physiologically-active compound). Preferably the biocompatible polymeric material is also biodegradable. In non-limiting embodiments, the shells typically have diameters in a range of 50-150 nm.

The MNPs of the presently disclosed and claimed inventive concepts preferably comprise major diameters in the range of 2-500 nm. More particularly the MNPs comprise major diameters, including, but not limited to, the ranges of 2-5 nm, 5-10 nm, 10-20 nm, 20-30 nm, 30-40 nm, 40-50 nm, 50-60 nm, 60-70 nm, 70-80 nm, 80-90 nm, 90-100 nm, 100-110 nm, 110-120 nm, 120-130 nm, 130-140 nm, 140-150 nm, 150-160 nm, 160-170 nm, 170-180 nm, 180-190 nm, 190-200 nm, 200-210 nm, 210-220 nm, 220-230 nm, 230-240 nm, 240-250 nm, 250-260 nm, 260-270 nm, 270-280 nm, 280-290 nm, 290-300 nm, 300-310 nm, 310-320 nm, 320-330 nm, 330-340 nm, 340-350 nm, 350-360 nm, 360-370 nm, 370-380 nm, 380-390 nm, 390-400 nm, 400-410 nm, 410-420 nm, 420-430 nm, 430-440 nm, 440-450 nm, 450-460 nm, 460-470 nm, 470-480 nm, 480-490 nm, or 490-500 nm and combinations thereof. In certain embodiments the major diameters are large enough to avoid uptake in the liver but are small enough to avoid filtration in the spleen (e.g., 100-200 nm).

The MNP cores may be constructed of (but are not limited to) $Fe_3O_4$ (magnetite), gamma-$Fe_2O_3$ (maghemite), alpha-$Fe_2O_3$ (hematite), FeNi, FePt, or Fe—CoNi alloy. Preferably the magnetically-susceptible cores of the MNPs are superparamagnetic, that is, they are non-magnetic unless exposed to (placed within) an external magnetic field.

In one non-limiting embodiment, MNPs carrying one or more therapeutic neurotoxicants (e.g., botulinum toxin-A: BtA) are magnetically targeted to one, two, three or four of the major atrial GP in the heart. BtA, for example, is known to inhibit neurotransmitter release at the synapse (up to 3-6 months)[45,49] without permanent injury to autonomic neurons or myocardium. This approach is designed to inhibit the release of the primary neurotransmitter, acetylcholine, that facilitates the initiation and maintenance of AF in order to allow the atria to cease the vicious cycle of atrial remodeling which allows AF to perpetuate itself.[50] Further, using this approach, collateral damage to the atrial myocardium and intrinsic CANS is minimized. The magnetic targeting approach described herein is safer and substantially less expensive than catheter or surgical ablation and preferably prevents or inhibits the progression from paroxysmal to persistent AF, which carries much higher risks of morbidities such as stroke. In a preferred embodiment, a focused external magnetic field is used to concentrate intravascularly-injected MNPs in one or more of the major atrial GP to treat patients with AF. Where the MNPs are described herein as being targeted to a GP, it is intended to refer to targeting MNPs to a portion or region of the heart which contains the GP, as well as referring to specifically targeting the GP itself. Further where the treatment is described as applying a magnetic field to the GP, it is intended to refer to applying a magnetic field to a portion or region of the heart which contains the GP, as well as referring to applying the magnetic field specifically to the GP itself.

As described herein, in one non-limiting embodiment of the presently disclosed and claimed inventive concepts, the goal was targeted drug delivery to the GP in order to treat AF. Superparamagnetic nanoparticles (MNP) containing a magnetite core, a thermo-responsive hydrogel matrix (polymeric shell) and a payload were synthesized and functionalized (with a drug or treatment compound). In one embodiment, a neurotoxic agent, N-isopropyl acrylamide monomer (NIPA-M), was incorporated into the hydrogel matrix as the payload. In the presence of an external magnetic field, this construct enabled magnetic capture of the MNP at the targeted GP site and allowed the payload (NIPA-M) to be released into that epicardial site to ablate the neural elements in the GP. In an alternate embodiment, the payload was the neurotoxicant botulinum toxin-alpha (BtA).

Thus, a preferred embodiment of the presently disclosed and claimed inventive concepts comprise using a magnetically targetable particle comprising: (a) a superparamagnetic component; (b) a temperature sensitive biocompatible polymer shell or coating; and (c) a biologically active agent, preferably a neurotoxin or neurotoxicant, incorporated into the shell.

The term "coating" or "shell", as used herein, includes coatings that completely cover a surface, or a portion thereof (e.g., continuous coatings, including those that form films on the surface), as well as coatings that may only partially cover a surface, such as those coatings that after drying leave gaps in coverage on a surface (e.g., discontinuous coatings). The later category of coatings may include, but is not limited to a network of covered and uncovered portions.

In a preferred embodiment, the presently disclosed and claimed inventive concepts are methods for the in vivo delivery of a biologically active agent to the heart, comprising: (a) suspending a superpara-magnetically targetable nanoparticle (MNP) in a vehicle for injection; (b) injecting the vehicle loaded with the MNP into a patient; and (c) establishing a magnetic field and gradient of appropriate strength and magnitude sufficient to guide and retain a portion of the magnetically targetable particles at a site of interest, preferably a portion of the heart.

In particularly preferred versions, the bioactive agent (i.e., neurotoxin or neurosuppressant) of the presently disclosed and claimed inventive concepts comprise N-isopropyl acrylamide monomer (NIPA-M), botulinum toxin-A (BtA), hemicholinium-3 (to block choline uptake at presynaptic cholinergic terminals in the GP and disrupt cholinergic signaling), 192-IgG-saporin (to induce apoptosis in neurons in GP expressing p75 neurotrophin receptor and eliminate signaling in those neurons), 192-IgG-toxin (wherein the toxin component is any cholinergic-neuron-destroying factor), 6-hydroxydopamine (to lesion catecholaminergic neurons in GP and disrupt adrenergic signaling), or propylbenzyl choline mustard (an irreversible antagonist for muscarinic receptors, to cause long-term block of cholinergic signaling in GP).

Exemplary bioactive agent loaded particles may comprise, for example, 0.1-50% by weight of bioactive agent (e.g., drug), 5-50% of magnetic core by weight, and 5-75% of polymer shell by weight.

The term "biocompatible polymer" as used herein is meant to include any synthetic and/or natural polymer that can be used in vivo as the shell or coating which surrounds the magnetic core of the MNPs used herein.

The biocompatible polymer may be bioinert and/or biodegradable. Some non-limiting examples of biocompatible polymers are polylactides, polyglycolides, polycaprolactones, polydioxanones, polycarbonates, polyhydroxybutyrates, polyalkylene oxalates, polyanhydrides, polyamides, polyacrylic acid, polyoxamers, polyesteramides, polyurethanes, polyacetals, polyorthocarbonates, polyphosphazenes, polyhydroxyvalerates, polyalkylene succinates, poly(malic acid), poly(amino acids), alginate, agarose, chitin, chitosan, gelatin, collagen, dextran, proteins, and polyorthoesters, and copolymers, terpolymers and combinations and mixtures thereof.

The biocompatible polymers of the presently disclosed and claimed inventive concepts can be prepared in the form of matrices. Matrices are polymeric networks. One type of polymeric matrix is a hydrogel, which can be defined as a water-containing polymeric network. The polymers used to prepare hydrogels can be based on a variety of monomer types, such as those based on methacrylic and acrylic ester monomers, acrylamide (methacrylamide) monomers, and N-vinyl-2-pyrrolidone. Hydrogels can also be based on polymers such as starch, ethylene glycol, hyaluran, heparosan, chitose, and/or cellulose. To form a hydrogel, monomers are typically crosslinked with crosslinking agents such as ethylene dimethacrylate, N,N-methylenediacrylamide, methylene bis (4-phenyl isocyanate), epichlarohydin glutaraldehyde, ethylene dimethacrylate, divinylbenzene, and allyl methacrylate. Hydrogels can also be based on polymers such as starch, ethylene glycol, hyaluran, chitose, and/or cellulose. In addition, hydrogels can be formed from mixtures of monomers and polymers.

Another type of polymeric network used in the biocompatible polymers used herein can be formed from more hydrophobic monomers and/or macromers. Matrices formed from these materials generally exclude water. Polymers used to prepare hydrophobic matrices can be based on a variety of monomer types such as alkyl acrylates and methacrylates, and polyester-forming monomers such as ϵ-caprolactone, glycolide, lactic acid, glycolic acid, and lactide. When formulated for use in an aqueous environment, these materials do not need to be crosslinked, but they can be crosslinked with standard agents such as divinyl benzene. Hydrophobic matrices can also be formed from reactions of macromers bearing the appropriate reactive groups such as the reaction of diisocyanate macromers with dihydroxy macromers, and the reaction of diepoxy-containing macromers with dianhydride or diamine-containing macromers.

The biocompatible polymers as noted elsewhere herein, may be, for example, biodegradable, bioresorbable, bioinert, and/or biostable. Bioresorbable hydrogel-forming polymers are generally naturally occurring polymers such as polysaccharides, examples of which include, but are not limited to, hyaluronic acid, starch, dextran, alginate, heparin, and chitosan; and proteins (and other polyamino acids), examples of which include but are not limited to gelatin, collagen, fibronectin, laminin, albumin and active peptide domains thereof and combinations thereof. Matrices formed from these materials degrade under physiological conditions, generally via enzyme-mediated hydrolysis.

Bioresorbable matrix-forming biocompatible polymers which can be used herein are generally synthetic polymers prepared via condensation polymerization of one or more monomers. Matrix-forming polymers of this type include, but are not limited to, polylactide (PLA), polyglycolide (PGA), polylactide-co-glycolide (PLGA), polycaprolactone (PCL), as well as copolymers of these materials, polyanhydrides, and polyortho esters, and combinations thereof.

Biostable or bioinert hydrogel matrix-forming polymers which can be used herein as biocompatible polymers are generally synthetic or naturally occurring polymers which are soluble in water, matrices of which are hydrogels or water-containing gels. Examples of this type of polymer include, but are not limited to, polyvinylpyrrolidone (PVP), polyethylene glycol (PEG), polyethylene oxide (PEO), polyacrylamide (PAA), polyvinyl alcohol (PVA), and combinations thereof.

Biostable or bioinert matrix-forming polymers which can be used herein as biocompatible polymers are generally synthetic polymers formed from hydrophobic monomers such as methyl methacrylate, butyl methacrylate, dimethyl siloxanes, and the like. These polymer materials generally do not possess significant water solubility but can be formulated as neat liquids which form strong matrices upon activation. It is also possible to synthesize polymers which contain both hydrophilic and hydrophobic monomers.

The biocompatible polymers can optionally provide a number of desirable functions or attributes. The polymers can be provided with water soluble regions, biodegradable regions, hydrophobic regions, as well as polymerizable regions.

In particularly preferred embodiments, the biocompatible polymer of the coating or shell of the presently disclosed and claimed inventive concepts may comprise, but is not limited to: poly(glycolic acid), poly(DL-lactic acid), poly(lactic acid-co-glycolic acid) copolymer, poly(ε-caprolactone), the poly (alkylcyanoacrylate) family, poly(isobutylcyanoacrylate), poly(ethylcyanoacrylate), polyethylenimine, poly(β-aminoesters), quaternary ammonium polysaccharides, poly(N-isopropylacrylamide i.e., PNIPA-Am), poly(N-isopropylmethacrylamide-co-acrylamide) copolymer, polyhydroxybutyrate, poly(ester-amide), poly(methylidene malonate), polyglutaraldehyde, poly(N-isopropylacrylamide)/poly (ethyleneimine) copolymer, PNIPA-Am/poly[N-(2-hydroxypropyl) methacrylamide] copolymer, PNIPA-Am-co-acrylamide-block-polyallylamine copolymer, PNIPA-Am-co-methylmethacrylate-co-methacrylic acid, poly[2-dimethyl(aminoethyl)methacrylate] (PDMAEM), PNIPA-Am/PDMAEM copolymer, PNIPA-Am-co-DMSO copolymer, PNIPA-Am-co-N,N-dimethylaminopropyl acrylamide-co-butylmethacrylate copolymer, poly(methacrylic acid-co-hydroxyethyl methacrylate copolymer, polyvinyl-benzyl-o-β-galactopyranosyl-D-glucosamide copolymer, Polyethylene glycol (PEG), PEG-silane copolymer, Fluid MAG®, poly(N,N-dimethylacrylamide), Pluronic F127®, carboxymethyl Dextron®, PEGylated amphiphilic triblock copolymer, gum Arabic, gum tragacanth, 2-(acetoacetoxy) ethyl methacrylate, poly(ethylene)glycol methylether methacrylate, chitosan triphosphate, chitosan triphosphate-hyaluronic acid, polyvinyl acetate, poly(vinylpyrrolidone), $SiO_2$-polymethylmethacrylate, poly [oligo(ethyleneglycol) methacrylate-co-methacrylic acid], poly(N-vinylacetamide) (NVA), PNIPAAm-co-NVA copolymer, Dextron-poly(ε-caprolactone)-2-hydroxyethyl methacylate-PNIPAAm copolymer, PNIPAAm-PEG copolymer, poly(ethyl-2-cyanocrylate), poly(butylcyanoacrylate), poly(hexylcyanoacrylate), poly(octylcyanoacrylate), heparin compounds, hyaluronic acid, and poly(3-(trimethoxysilyl)propyl methacrylate-r-PEG methyl ether methacrylate-r-N-acryloxysuccinimide), and combinations of the above.

Preferably, one or more biologically active (bioactive) agents are incorporated with the polymer shell of the particles for delivery to specific sites under control of a magnetic field. A biologically active agent can be incorporated with the particle by a linkage. For example, a biologically active agent can be covalently linked to the polymer, either directly or through a linker. Alternatively, a biologically active agent can be ionically linked, or associated, to the polymer, either directly or through a linker or a derivative. The bioactive agents can also be embedded, contained within, adsorbed or absorbed on or within a polymer matrix, such as a hydrogel or a block copolymer, and permitted to diffuse from the particle at a controlled rate. The rate of diffusion of the biologically active agent can be controlled by varying the composition of the matrix and by varying the magnetic filed as discussed elsewhere herein.

The term "biologically active agent" "bioactive drug", "bioactive agent", "active agent" or "active ingredient" is meant to include, but is not limited to, any material having diagnostic and/or therapeutic properties including, but not limited to, small molecules, macromolecules, peptides, polypeptides, proteins, enzymes, DNA, RNA, genes, lipids, carbohydrates, glycoproteins, lipoproteins, iron oxides, or radionuclides. In non-limiting examples, these compounds may be neurotoxic, neurotoxicants, and/or neurosuppressants, as well as antimetabolitic, antifungal, antiinflammatory, antitumoral, antiinfectious, antibiotic, nutritive, agonistic, and/or antagonistic.

In certain embodiments, the MNPs are in the shape of a cylinder, a cylindrical rod, a worm, a circular disc, a sphere, an ovoid, an irregular shape or a combination thereof.

In a particularly preferred version of the method of the presently disclosed and claimed inventive concepts, once the MNPs have been magnetically drawn to the desired location in the heart, for example one or more of the atrial GP, the magnetic force applied to the superparamagnetic nanoparticles can be changed from static to oscillating (e.g., alternating) which causes the MNPs to become warmer, above normal physiologic temperatures (i.e., above 37° C.) causing an increase in the release of the bioactive agent from the coating of the MNPs in a phenomenon referred to herein as "magnetothermally-triggered release." This may be induced for example at 100-300 Hz.

In regard to the types of magnets which can be used herein, the pole face field strength is preferably 400 milli-Tesla (mT) to 700 mT. The gradient is preferably 2-10 T/meter. When the magnet is an electromagnet, the duty cycle of the electromagnet can range from 10% to 33% for example. Its output can be a square wave or a balanced wave form, equal upward and downward, representing a change in polarity. In regard to the magnetic field strength to be applied at the MNP capture point in the coronary micro-circulation, the preferred range is 100 mT to 300 mT. Ranges of frequencies of oscillations to be applied include, by way of example but not by way of limitation, 100-200 Hz or 200-400 Hz for heating of local tissue in the vicinity of the nanoparticles that were targeted to that site.

In an alternative version of the presently disclosed and claimed inventive concepts, MNPs without a therapeutic compound (bioactive drug) may be used, and the targeted neurons of the GP of the heart may be killed by magnetically heating the MNPs to a temperature at which myocardial tissue dies, such as 49°-55° C. (where normal physiologic temperature is ≤38° C.). This can be induced by exposure of the MNPs to a frequency of 200-400 Hz, for example.

In a secondary aspect of the presently disclosed and claimed inventive concepts, the MNPs can gather as clumps within blood vessels of the fat pads of the GPs, causing ischemia of the tissues supplied by said blood vessels and thereby killing all or some of the neurons in the affected tissues. The propensity for causing the MNPs to aggregate and clump and clog a blood vessel (embolism) can be increased by increasing the magnetic field strength and/or the magnetic field gradient at that preferred embolic site. The size of the aggregates may be for example 100-300-900 nm in diameter, and the sizes of agglomerations of the aggregates in microvessels are the size of the inside diameter of the vessels, e.g., 1-10 micrometers in width, for example, and 1 μm to 3 mm, for example, in length.

In general, during a single treatment comprising the method of the presently disclosed and claimed inventive concepts, the magnetic field is applied to the specific portions of the heart for durations of from 10 minutes to 6 hours, and more preferably from 20 minutes to 4 hours and still more preferably from 30 minutes to two hours, although it will be understood that the magnetic field can be applied, for example for 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355 or 360 minutes, or any integeric minute there within.

In another preferred embodiment, the magnetic field is applied to the MNPs for targeting the MNPs in association with concurrent application of Magnetic Resonance Imaging (MRI), for example in a manner shown in U.S. Published Patent Application 2010/0079142, the entirety of which is incorporated by reference herein.

In one embodiment, the MNPs are administered in a treatment protocol comprising a first treatment comprising one or two doses for example, followed by another treatment in 2-8 months (preferably 4-6 months), optionally followed by two to three similar treatments administered after similar durations of time.

In one embodiment, the concentration of the active agent of the MNPs may be, but is not limited to, 1 ng-10 mg per injection (dose). In one embodiment, BtA is provided in a range of 2-10 ng, while NIPA is provided in a range of 1-10 mg/dose.

The concentration of the BtA provided may be in a range of, for example, 1-50 nM.

In a preferred version of the presently disclosed and claimed inventive concepts, the magnetic field applied to the MNPs causes the MNPs to move through the myocardial tissues at a velocity in a range of, but not limited to, 0.01-0.1 mm/min. In specific embodiments the velocity may be 0.01, 0.02, 0.03, 0.04, 0.05, 0.06, 0.07, 0.08, 0.09, or 0.10 mm/min.

Additionally, the contractions of the heart myocardium while the heart is beating also facilitate movement of the drug, and the MNPs, through the myocardium, in the direction of the stronger magnetic field and down the field gradient.

In one embodiment of the presently disclosed and claimed inventive concepts, the magnetic field may be applied directly to the myocardium of the heart, e.g., at the fat pad surface of the GP. This is referred to "implant-associated magnetic targeted drug delivery." Alternatively, the magnetic field may be applied externally to the body, on or near the surface of the chest.

In a preferred environment, the permanent magnet or electromagnet pulls the MNP into the region of the heart where body temperature causes the shell (e.g., PNIPA-AAm) to release the bioactive agent (e.g., BtA). This heat lability is a property of the particle's polymer shell or matrix (e.g., PNIPA-AAm).

As noted above, once the nanoparticles are pulled into position near the targeted region, e.g., the ganglionated plexi, the electromagnet can be adjusted to present an alternating magnetic field of known frequencies to cause warming of the MNPs by oscillating the magnetite (or other ferrous material in the core), then using the magnet to accelerate the release of the bioactive agent for a controlled release of the therapeutic. Furthermore, the tissue in the vicinity of the ganglionated plexi is warmed by the oscillation of the nanoparticles. Excessive warming, also has a "lesioning" effect on nerve tissue (more sensitive than heart cells).

The quantitative denervation, which changes the autonomic balance of neural control of cardiac rhythm, is accomplished both by release of the neurotoxic chemical, e.g., NIPA monomer, or BtA, in the tissue of the ganglionated plexus (e.g., the ARGP) and additionally, optionally, by the embolization of the microvessels serving the GP. This embolization is caused by magnetic capture of the superparamagnetic nanoparticles carrying the compound in the vicinity of the GP so that blood flow to the GP is reduced and the neurons are reduced in their autonomic influence.

An implanted permanent magnet (e.g., a rare earth magnet such as NdFeB) can be placed on the surface of the GP on the surface of the heart to capture the nanoparticles as they reach the GP through a branch of the sinus nodal artery and hold those nanoparticles in position to allow for timed release of the bioactive agent. Additionally some of the nanoparticles will be pulled through walls of microcirculation into the extracellular space of the GP After the polymer shell exceeds the lower critical solution temperature (LCST), bioactive agent (e.g., neurosuppressant) is released from the polymer shell and (targeted) neuropathy will occur in the GP.

An internally positioned magnet can be implanted, for example, (1) by introducing a removable, permanent, magnet at the time of open chest heart surgery; (2) by introducing a magnet minimally invasive via thoracopy in the closed chest patient; and/or (3) by introducing a magnet by intravascular (venous) catheter in the closed chest patient.

In an alternate version, a Direct Current, externally positioned electromagnet is placed over an area of GP site on the chest of the patient in the following ways:

(1) an electromagnet is placed only over the surface of the heart with focused flux density (magnet strength) and magnetic gradient into the GP only; and/or (2) a magnetizable implant or a permanent magnet is placed over the GP at time of cardiac surgery or via thoracopy (to focus capture and localize external magnetic energy in to local flux gradients near the GP site).

In an alternate version, an Alternating Current, externally positioned electromagnet is placed over the GP site on the chest of the patient then alternating (+ then − or attraction then repelling) magnetic fields are provided to induce micromovements ("shaking" or oscillations) of the MNPs to cause them to heat and the hydrogel to contract and release its therapeutic payload to cause neurotoxic ablation of autonomic neurons in the targeted GP. This magnet is for the purpose of accelerating the heating of the MNPs and allowing particles to reach the LCST more rapidly for release of the bioactive agent "on command". This adds a quantitative ability for the timing of and amount of release of the agent, the longer and more intense the heating, the more bioactive agent is released from the polymer shell.

As noted, the heating of the polymer shell of the MNPs to the LCST of the polymer, either by magnetically-induced heating or heating by the intrinsic body temperature, will induce release of the active agent into the circulation. The level of heating necessary to reach the LCST can be established by the chemical formulation. The method preferred herein is to set the LCST by its formulation at body temperature, so that when the particles are warmed to about 38° C., they will begin to release the active agent. This keeps the solution stable at room temperature and the chemical payload (active agent) will not be released prematurely on the shelf. If warmed to the LCST by magnetic oscillations, the release will be accelerated and under the control of the magnet. If the particles are warmed above the LCST, this will assure that all the payload is released. As noted elsewhere herein. if the tissue in the region of the GP is heated to 48-50° C. then neurons therein will begin to die (before cardiac cells).

The external source of a magnetic field of the presently disclosed and claimed inventive concepts are capable of (i) magnetizing the superparamagnetic particle and (ii) increasing a degree of magnetization of the MNP and thereby increasing the force of contraction. Those skilled in the art using guidance provided in this disclosure will be able to select the proper magnetic source and its capabilities without undue experimentation. The preferred external source is an electromagnet.

EXAMPLES

While the presently disclosed and claimed inventive concepts will now be described in connection with certain preferred embodiments in the following examples so that aspects thereof may be more fully understood and appreciated, it is not intended to limit the presently disclosed and claimed inventive concepts to these particular embodiments. On the contrary, it is intended to cover all alternatives, modifications and equivalents as may be included within the scope of the presently disclosed inventive concepts as defined by the appended claims. Thus, the following examples, will serve to illustrate the practice of this presently disclosed and claimed inventive concepts, it being understood that the particulars shown are by way of example and for purposes of illustrative discussion of preferred embodiments of the presently disclosed and claimed inventive concepts only and are presented in the cause of providing what is believed to be the most useful and readily understood description of formulation procedures as well as of the principles and conceptual aspects of the presently disclosed and claimed inventive concepts.

Catheterization of the heart, into the right coronary artery with access to the sinus nodal artery can be made in the subject and is done readily every day by interventionalists performing angiography of the coronary vessels. Such a catheter can be used to release a dosage of a solution of the MNPs that will flow downstream to target the cardiac tissue containing the Anterior Right Ganglionated Plexus (or other GP). At the ARGP, or other GP, a magnetic field and gradient will be present, caused either by a permanent magnet or electromagnet, either internal in the chest of a patient or external, i.e., outside the chest of a patient as discussed elsewhere herein.

The MNPs in the specific examples described below comprise in one embodiment a composite containing magnetite, a biocompatible, magnetically susceptible iron oxide that is superparamagnetic because of its size. The size in one embodiment is about 10-15 nm. Single or multiple magnetite MNPs are encapsulated into a single larger nanoparticle by a coating of pNIPA-AAm, which contains a bioactive agent such as NIPA-M which will be released once in the blood, over specified time periods determined by chemical means. So when the NIPA-M-containing magnetite nanoparticles are in the region of the ARGP, they respond to the magnetic field and gradient and are captured in the ARGP microcirculation subserving the ARGP, and are held there as long as there is a magnetic field and gradient present. Once magnetically captured (by magnetic targeting), the particles are pulled from the coronary microcirculation into the epicardium containing the GP, toward the pole face of the magnet. Next the NIPA-M begins to be released and because it is cytotoxic, and noteworthy, neurotoxic, it will begin to decrease the autonomic neural activity in the ARGP. Additionally, since the blood flow to the ARGP is reduced (depending on the amount of magnetite nanoparticles magnetically trapped in the microvasculature), this targeted ischemia of the ARGP also reduces the neural activity of the ARGP, adding to the neurotoxic action from the released NIPA-M. Thus, there is a unique dual means for quantitatively reducing ARGP activity. A third method for suppressing GP activity is the use of alternating current applied to the GP to oscillate the MNPs, thereby producing heating and raising adjacent neural tissue temperature to an average of 48° C. for a period of 90 seconds, thereby permanently damaging neural function.

Example 1

Methods

In a first version of the presently disclosed and claimed inventive concepts (as discussed in detail below), superparamagnetic nanoparticles (MNPs) made of a core of $Fe_3O_4$, a shell of a thermo-responsive polymeric hydrogel, and a neurotoxic agent (NIPA-M monomer) were synthesized and functionalized. An external magnet, placed on the fat pad containing GP, was used to navigate and concentrate the MNPs at the largest ganglionated plexus in the mammalian heart. The electrophysiological function of this ganglionated plexus was markedly suppressed by trans-coronary delivery of the magnetic nanoparticles. Histological studies revealed Prussian blue (stained) iron aggregates in the targeted ganglionated plexus.

Synthesis and Functionalization of Superparamagnetic Nanoparticles

To synthesize the MNPs, the core (e.g., magnetite, $Fe_3O_4$) was formed by co-precipitation of ferrous and ferric salts in the presence of basic solution and docusate sodium salt as a surfactant developed previously.[51,52] Then, the magnetic nanoparticles were coated with vinyltrimethoxysilane via acid catalyst hydrolysis followed by electrophilic substitution on the surface of the MNP.[52,53] Poly-N-isopropylacrylamide-co-acrylamide (pNIPA-AAm), a thermo-responsive hydrogel, was then polymerized on the magnetic core via a silane coupling agent and radical polymerization method. This process allows a strong attachment of the magnetic core with the polymeric hydrogel matrix (shell) thereby preventing the core of the MNP from diffusing out of the polymer shell and also permits the encapsulation of a bioactive agent (e.g., NIPA-M). The lower critical solution temperature (LCST), the temperature above which the hydrogel contracts and disintegrates, of the hydrogel used in the present study was formulated at 37° C., allowing for enhanced drug release only at the body temperature. Of note, although the polymeric NIPA (pNIPA-AAm) was an essential element of the hydrogel shell of our nanoparticles, pNIPA-AAm, polymer, unlike NIPA monomer, is not neurotoxic.[54]

The size of the pNIPA-AAm coated MNP was evaluated by transmission electron microscopy (TEM) and a laser scattering particle sizer as previously described.[52] To assess the temperature sensitivity of our polymer shell, optical transmittance of the MNP solution (2 mg/ml) at various temperatures (15-50° C. with the rate of 1° C./min) was measured at 650 nm with a Cary-50 UV-Vis spectrophotometer, which was coupled with a PCB-150 circulating water bath as described previously.[52,55]

For drug loading, the freeze-dried pNIPA-AAm coated MNP (2.5 mg/ml) were resuspended and incubated with NIPA-M (drug; 2.5 mg/ml) in PBS at 4° C. for 3 days on a shaker. After incubation, drug loaded MNP were collected using a magnet. The supernatant was stored at −20° C. for determination of loading efficiency indirectly. The loading efficiency is defined as the difference between the total amount of added NIPA-M and the amount present in the supernatant, divided by the total amount of added NIPA-M.[56]

To study the drug release kinetics of NIPA-M, nanoparticles were suspended in PBS solution at 25° C. and 37° C. for 14 days on a shaker with gentle mixing. At designated time intervals, MNP were captured against the side of a tube by a magnet and the supernatant was removed from each sample and stored at −20° C. for later analysis. After experiments, the amount of NIPA-M was determined as described previously.[56] In brief, a UV-Vis spectrophotometer was used for the measurement of NIPA-M released from the nanoparticles over the time. To generate a standard curve of NIPA-M concentrations against the absorbance, NIPA-M standards were prepared by dissolving known amount of NIPA-M in PBS and by preparing serial dilutions. The NIPA-M standards and NIPA-M released in each sample (200 µl) were added to a 96-well plate (transparent and compatible for UV wavelengths). The plate was read at 270 nm for absorbance using a UV-Vis spectrophotometer. The standard curve was plotted and the absorbance readings of samples were determined against the standard curve. Finally, the NIPA-M release curve, cumulative NIPA-M release (% of loading) vs. time (hours), was plotted.

Animal Preparation and In Vivo Studies

Twenty-three adult mongrel dogs, weighing 20-25 kg, were anesthetized with Na-pentobarbital. Positive pressure ventilation was instituted using a respirator. Core temperature was maintained at 37.0±1.0° C. The chest was opened via a right lateral thoracotomy at the $4^{th}$ intercostal space. The pericardium was incised and also reflected to expose the right atrium (FIG. 1). Electrograms were recorded from the His bundle region, right atrium, right superior and inferior pulmonary veins. At the base of the right pulmonary veins adjacent to the caudal end of the sino-atrial node, there is a distinct fat pad known to contain the ARGP. At the junction of the inferior vena cava and both atria, there is a fat pad which contains the inferior right GP (IRGP). High frequency stimulation (HFS; 20 Hz, 0.1 ms, square pulse) was applied to both GPs at the voltage level which did not excite the atrium through a two-channel Grass stimulator (S88; Astro-Med, Warwick, Mass.) as previously described.[57] Prior studies have shown that the ARGP function could be assessed by the sinus rate slowing response elicited by ARGP stimulation while the IRGP function could be assessed during AF by the ventricular rate slowing response induced by IRGP stimulation.[58,59] At higher voltage levels, which varied from animal to animal, AF could be induced by stimulation of the ARGP or IRGP. The lowest voltage required to induce AF was determined to be the inducibility threshold for each dog, respectively. AF is defined as an irregular atrial rate faster than 500 beats per minutes associated with irregular atrioventricular conduction.

In 6 animals, 0.5 ml of MNP carrying 0.4 mg NIPA-M were injected into the ARGP via a 25-gauge needle attached to a polyethylene tube as previously described.[60] The maximal sinus rate slowing response induced by ARGP stimulation without causing AF was measured in the baseline state, 30 minutes, 60 minutes, 2 hours and 3 hours after MNP injection into the ARGP. In 4 other animals, a cylindrical permanent magnet (2600 gauss; surface area, 2 $cm^2$) was sutured to the epicardial surface of the fat pad containing the IRGP, but not ARGP, in order to capture the MNP. The circumflex coronary artery was cannulated and 1 ml of MNP that contained approximately 0.8 mg of NIPA-M was infused into the circumflex coronary artery over 3-4 minutes. Both the ARGP function and IRGP function as described above were assessed at the time intervals of 30, 60, and 120 minutes.

Two sets of control experiments were conducted in seven additional animals. In set 1, MNP containing the magnetic core and hydrogel shell but without the NIPA-M payload (N=4) were targeted to determine if suppression of the IRGP function occurred in the absence of NIPA-M with micro-embolization alone. In set 2, MNPs made of the hydrogel shell and NIPA-M payload but without the magnetic core (N=3) were infused to assess if magnetic targeting was essential for effecting AF inducibility. All control animals received trans-coronary delivery of the nanoparticles and electrophysiological studies were performed before and after the interventions.

In 6 other animals, 1.6 mg of NIPA-M (twice the amount of NIPA-M incorporated into one trans-coronary delivery) was directly injected into the left ventricle. NIPA-M used in these experiments was not incorporated into the hydrogel in order to simulate the greatest possible toxic challenge should the total NIPA-M dose be released instantly into the circulation from trans-coronary infusion. Serum samples before and 9.7±0.3 hours after NIPA-M injection were collected for paired analysis to assess renal and hepatic toxicity.

Histological Studies

In the experimental group, 3 of 4 dogs receiving MNP infusion into the circumflex artery, both the ARGP and IRGP and adjacent atrial tissue were excised for histological confirmation of targeted drug delivery to the IRGP. In the control group (MNPs without NIPA-M payload), IRGP and adjacent atrial tissue were excised for histological iron stain confirmation of targeted delivery to the IRGP. GP and atrial tissue were fixed in formalin and embedded in paraffin. Serial sections of the entire tissue block were performed. Prussian Blue stain was used to detect both ferric and ferrous salts which form the core of the MNPs.

Statistical Analysis

All data are presented as mean±standard error. The changes of the GP function, and AF threshold induced by GP stimulation at different time courses were evaluated by repeated measurements of ANOVA followed by the Tukey test for comparisons different time point after the application of MNP versus baseline. Statistical significance was defined as $P<0.05$.

Results

The Physical Properties of the Core-Shell Magnetic Nanoparticles.

Figure 2A:
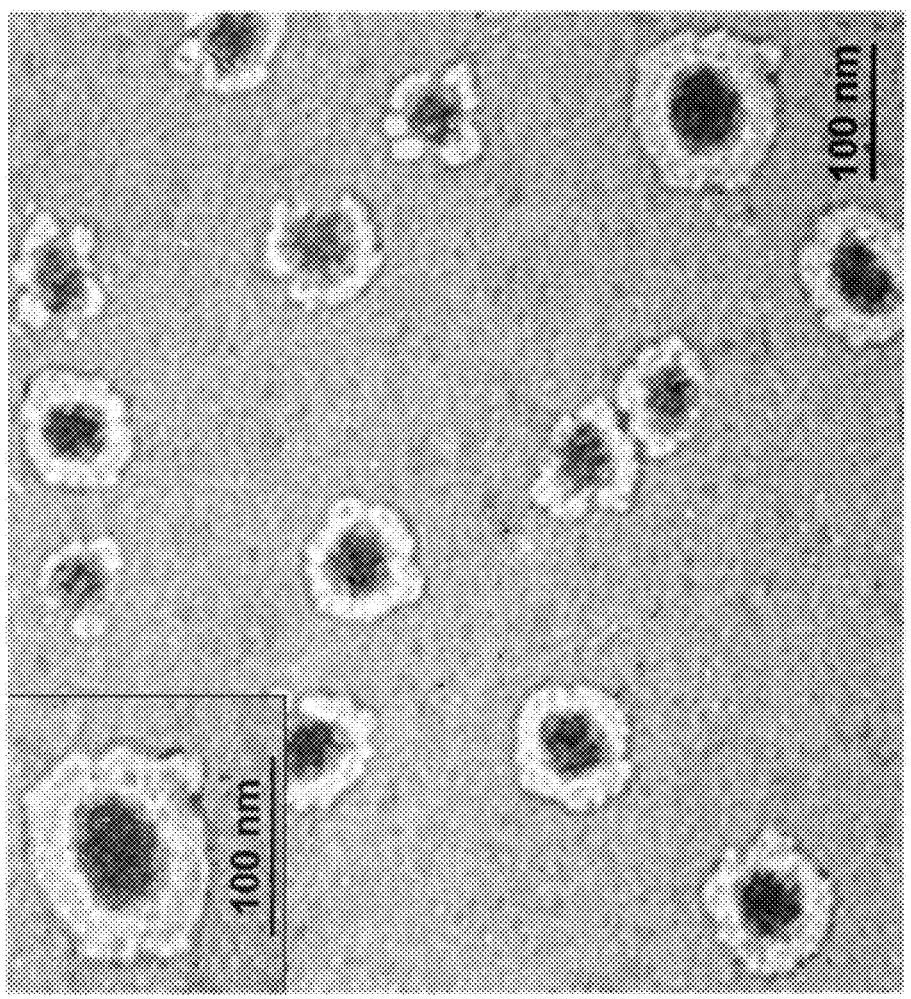
FIG. 2 (A) shows a transmission electron micrograph of (poly-N-isopropylacrylamide-co-acrylamide polymer) (pNIPA-AAm) coated superparamagnetic nanoparticles (MNPs). Each magnetic susceptible iron oxide core (dark center) of the MNP was surrounded by the polymeric shell layer (white layer surrounding the dark core).
FIG. 2(B) shows graphs of in vitro release profiles of N-isopropylacrylamide monomer (NIPA-M) from polymeric pNIPA-AAm-coated MNPs at 25° C. and 37° C. Curves in this figure present the cumulative percent releases of NIPA-M over 336 hours at 25° C. and 37° C. Inset graph: release kinetics in the first 4 hours.

The average size of the functionalized MNPs was determined using transmission and scanning electron micrograph. The average size of the MNPs coated with pNIPA-AAm was about 100 nm in diameter. FIG. 2A shows that each magnetic core (dark center) was surrounded by a polymeric shell layer (white layer surrounding the dark core). For drug loading studies, NIPA-M was added at a concentration of 2.5 mg/ml to the nanoparticle suspension as described in the METHODS section of Example 1. The loading efficiency of NIPA-M was found to be 38%, consistent with the efficiency described previously.[52,55]

The release kinetics at both 25° C. and 37° C. followed a parallel curvilinear course. Cumulative release of NIPA-M at 37° C. was approximately twice as much as that at 25° C. Importantly, nearly 30% of the NIPA-M was released within the first 2 hours at 37° C. (inset, FIG. 2B).

Microinjection of MNPs into the ARGP

Figure 3:
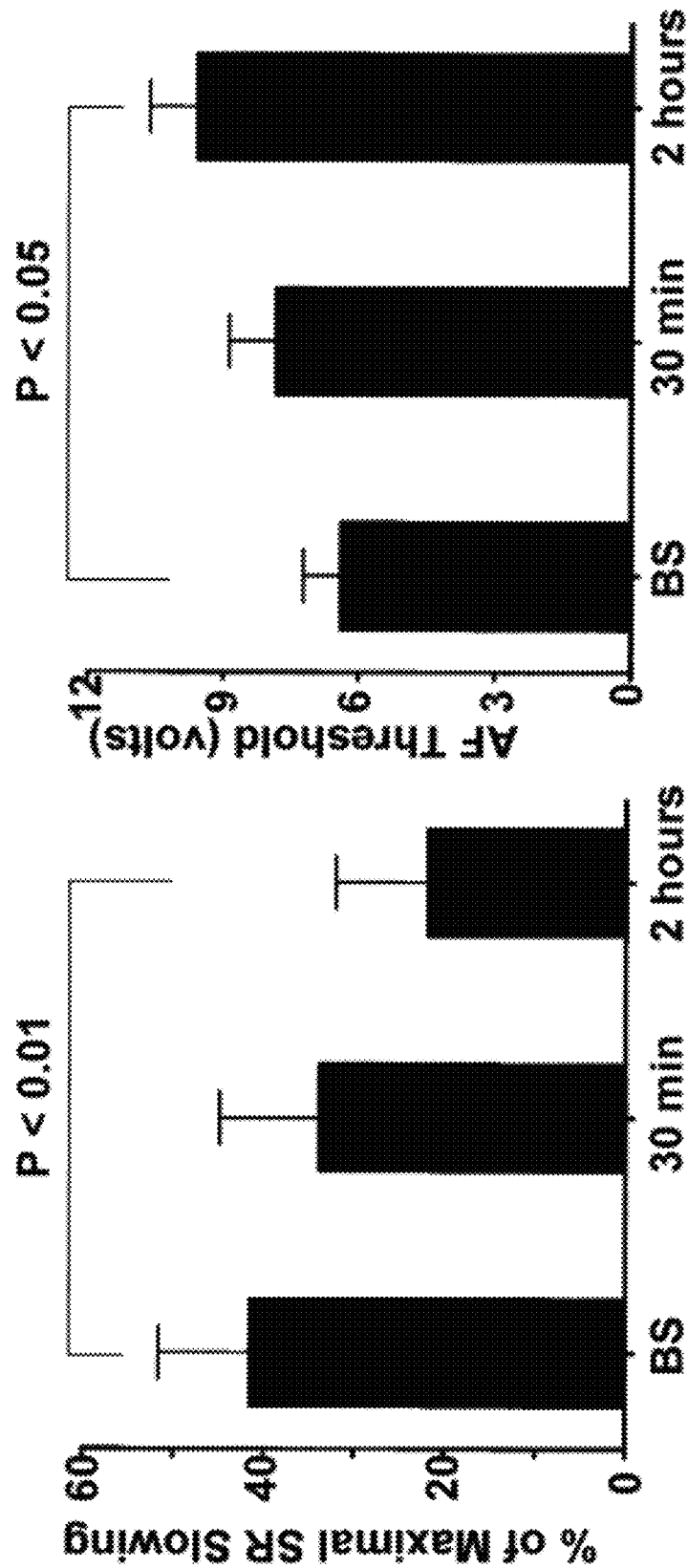
FIG. 3 shows decrease in sinus rate by ARGP stimulation. MNP carrying 0.4 mg NIPA-M were microinjected into the ARGP (N=6). Left. Two hours after the injection, the maximal decrease of sinus rate by ARGP stimulation was reduced from 40±8% to 21±9%. Right. AF threshold also significantly increased 2 hours after injection.

To examine the in vivo neurotoxic effect of the MNPs, 0.5 ml of MNP containing 0.4 mg NIPA-M was injected into the ARGP as described above. FIG. 3 (left panel) shows that the percent of maximal sinus rate slowing caused by ARGP stimulation without inducing AF. Before MNP injection, ARGP stimulation reduced the sinus rate by 40±8% while 2 hours after MNP injection, ARGP stimulation only exerted a maximal effect of 21±9% ($p<0.01$). The lowest voltage (threshold) of ARGP stimulation that induced AF was increased from 5.9±0.8V (baseline) to 10.2±0.9V (2 hours; $p<0.05$). The effects of ARGP suppression did not differ between 2 hours and 3 hours after MNP injection (data not shown). Therefore, subsequent experiments were conducted up to two hours after intra-coronary infusion of the MNPs.

Intra-Coronary Arterial Delivery of MNPs

Figure 4:
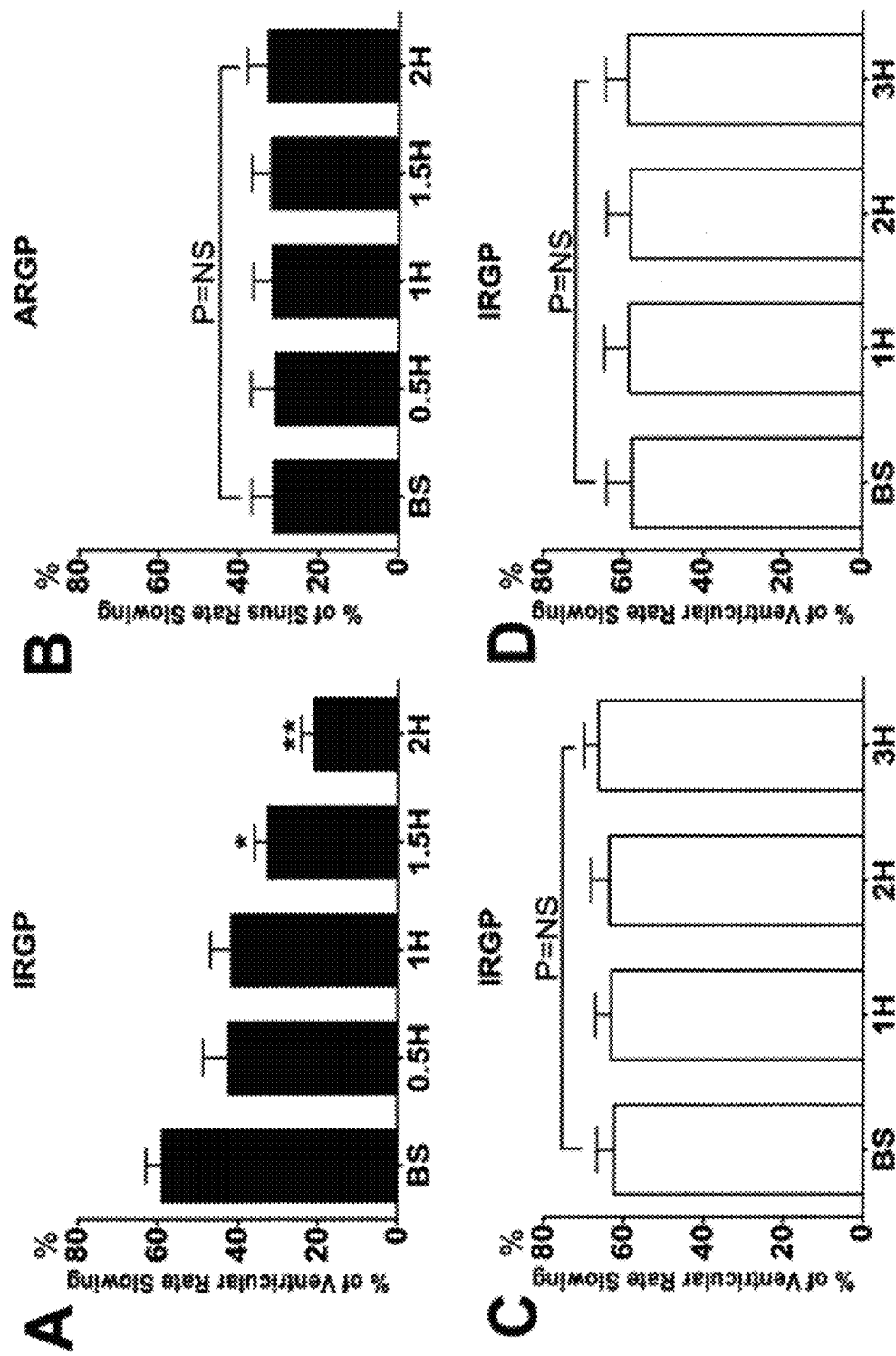
FIG. 4 shows changes in the GP function after infusion of MNPs into the circumflex coronary artery. (A) MNPs carrying 0.8 mg of NIPA-M (permanent magnet was placed above the atrial tissue containing the IRGP; N=4). The maximal ventricular rate slowing response induced by IRGP stimulation during AF was reduced from 57±8% (BS, baseline) to 33±3% (1.5 hours; p<0.05) and 20±8% (2 hours; p<0.01). In contrast, the ARGP (which did not have a magnetic force applied thereto) function, assessed by the maximal sinus rate slowing response induced by ARGP stimulation, was not altered. Control experiments: (C) After magnet was placed above the IRGP, animals received trans-coronary infusion of MNPs without NIPA-M (N=4) or (D) nanoparticles without the magnetic core (N=3).

In the four animals receiving infusion of MNPs into the circumflex coronary artery, the ARGP and IRGP functions were measured before and after MNP infusion. Before the administration of the MNPs, IRGP stimulation during AF slowed the ventricular rate by 57±8% but this effect was diminished to 33±3% ($p<0.05$) and 20±8% ($p<0.01$), 1.5 and 2 hours after infusion of the MNPs, respectively (FIG. 4, left panel). In contrast, the sinus rate slowing response induced by stimulation of the ARGP, where no magnet was placed, was not altered over a period of 2 hours (31±7% baseline; 33±8%, 2 hours; p>0.05).

In the four animals receiving MNPs without NIPA-M payload and the three animals receiving nanoparticles without the magnetic core, the IRGP function was not altered over 3 hours (FIG. 4C-D). In the six animals the receiving NIPA-M direct ventricular injection, the serum creatine, blood urea nitrogen (BUN), BUN/creatine ratio and alanine aminotransferase (ALT) did not change (before NIPA-M: creatinine=0.8±0.1 mmol/L, BUN=14.8±3.4 mmol/L, BUN/creatine=19.1±4.7, ALT=33.3±5.6 U/L. 9.7±0.3 hours after NIPA-M: 0.9±0.1 mmol/L, BUN=16.2±2.9 mmol/L, BUN/creatine=17.6±1.7, ALT=41.3±8.7 U/L; p>0.05 for all by paired t-test).

Figure 5:
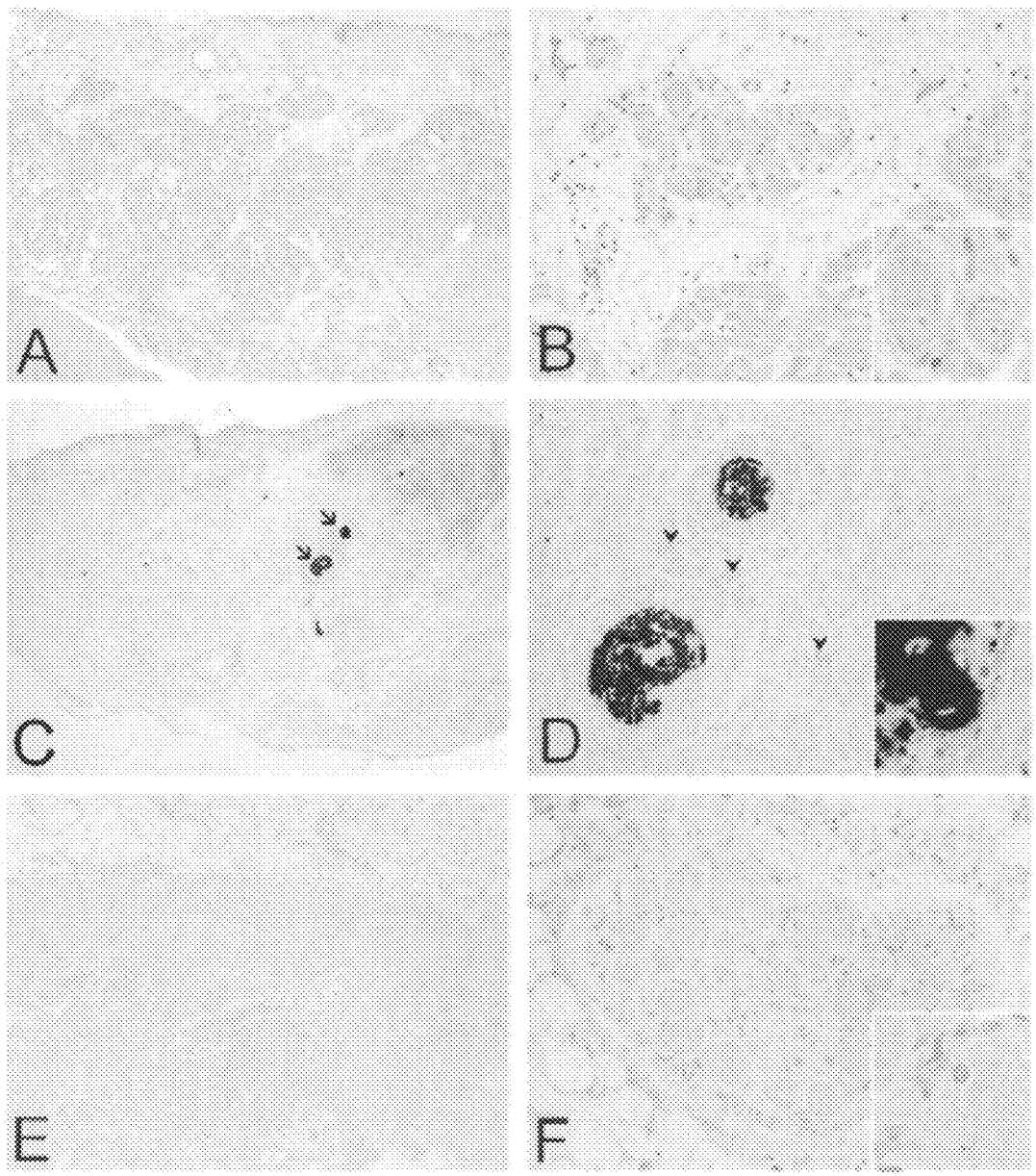
FIG. 5 shows micrographs of representative examples of the IRGP histology after intra-coronary arterial infusion of MNPs. (A) On low-magnification, a small amount of iron (Prussian blue staining iron oxide nanoparticle aggregates) is present, most notably in sub-epicardial adipose tissue. (B) Blue stained MNP aggregates are also present in ganglia. Most of the iron oxide-containing particles are present in the peri-ganglionic tissue (inset). (C) Intravascular MNP aggregated emboli (arrows) containing iron are present in some of the sections. (D) On high magnification, targeted MNP (iron depositions) are also present in the adipose tissue (arrow heads) around the blood vessels. High magnification of the iron containing thrombus is shown in the inset. (E) Similar iron oxide aggregates are noted in the adipose tissue of the control heart. (F) Iron oxide aggregates are also present in the ganglions of control heart. High magnification of the deposits is shown in the inset. Original magnifications for panel A, C, and E are 4×, for panel B, D, and F are 20×, for the insets are 60×.
Figure 6:
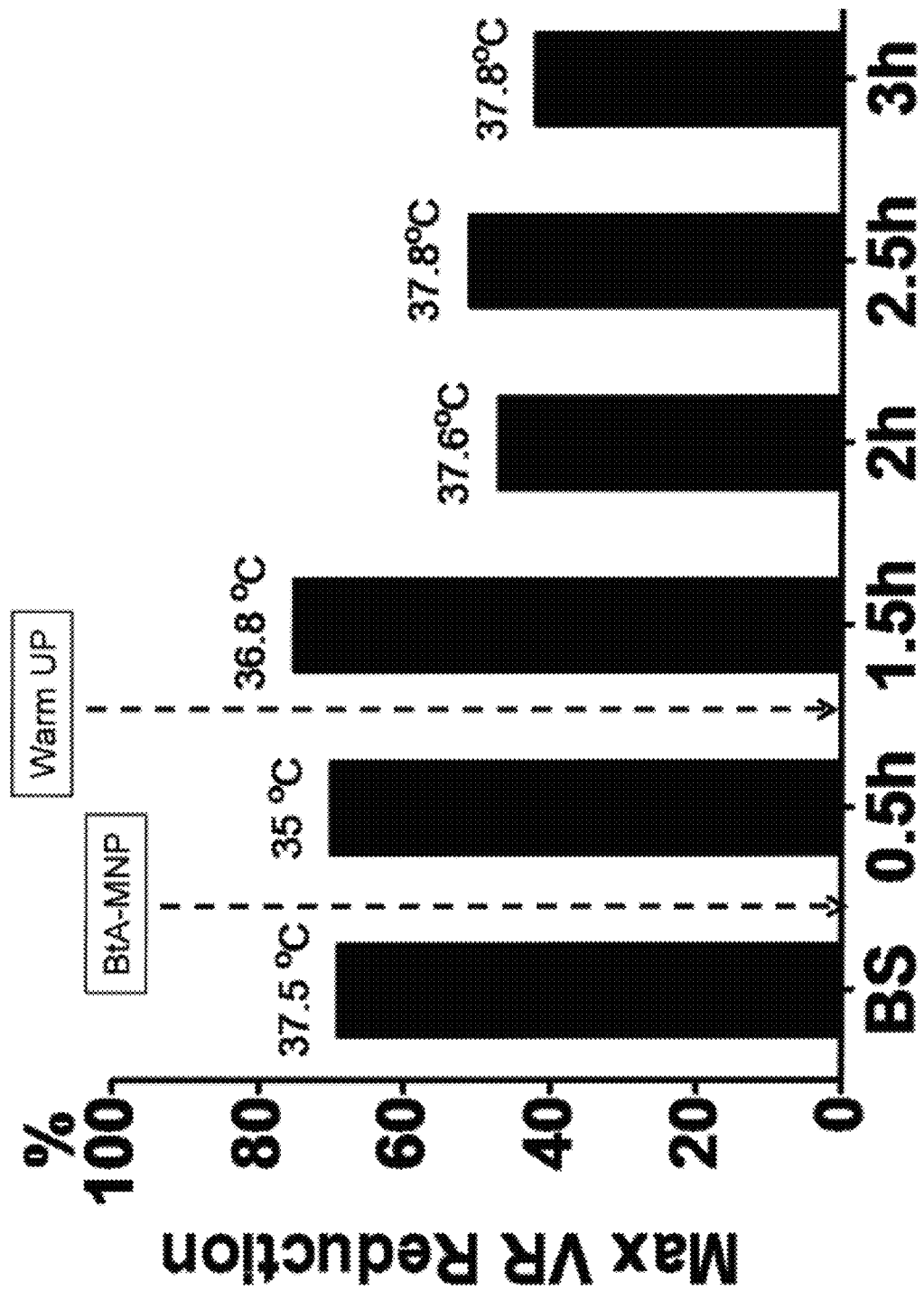
FIG. 6 is a graph showing suppression of IRGP function by BtA-MNP (botulinum toxin-alpha-MNPs). In this example, the IRGP function was suppressed within half an hour after the temperature was raised to >37° C. to release the payload.

Histological studies demonstrated small Prussian Blue (+) aggregates in the epicardial fat pad containing the IRGP but not the ARGP (FIG. 5A-B). In addition, large Prussian Blue (+) aggregates were found only in the micro-circulation of the IRGP but not in the ARGP, implying embolization of the micro-circulation of the IRGP by these large MNP aggregates (FIG. 5C-D). FIG. 5E-F showed that small Prussian Blue (+) aggregates in the epicardial fat pad containing the IRGP in the control group (MNPs without NIPA-M payload) as well. In contrast, only rare and faint Prussian Blue (+) reactions were found after serial histological sections of the ARGP were carefully examined (data not shown).

Discussion

Example 1 demonstrated that GP function can be suppressed by a targeted drug delivery system comprising MNPs comprising magnetite (core), a thermo-responsive pNIPA-AAm hydrogel matrix (shell), and a NIPA-M (neurotoxin) payload. Electrophysiological and histological studies verified that the external magnetic force was capable of pulling these MNPs out of the microcirculation to desired locations of the heart and inhibiting the function of the targeted neural tissue.

Figure 2B:
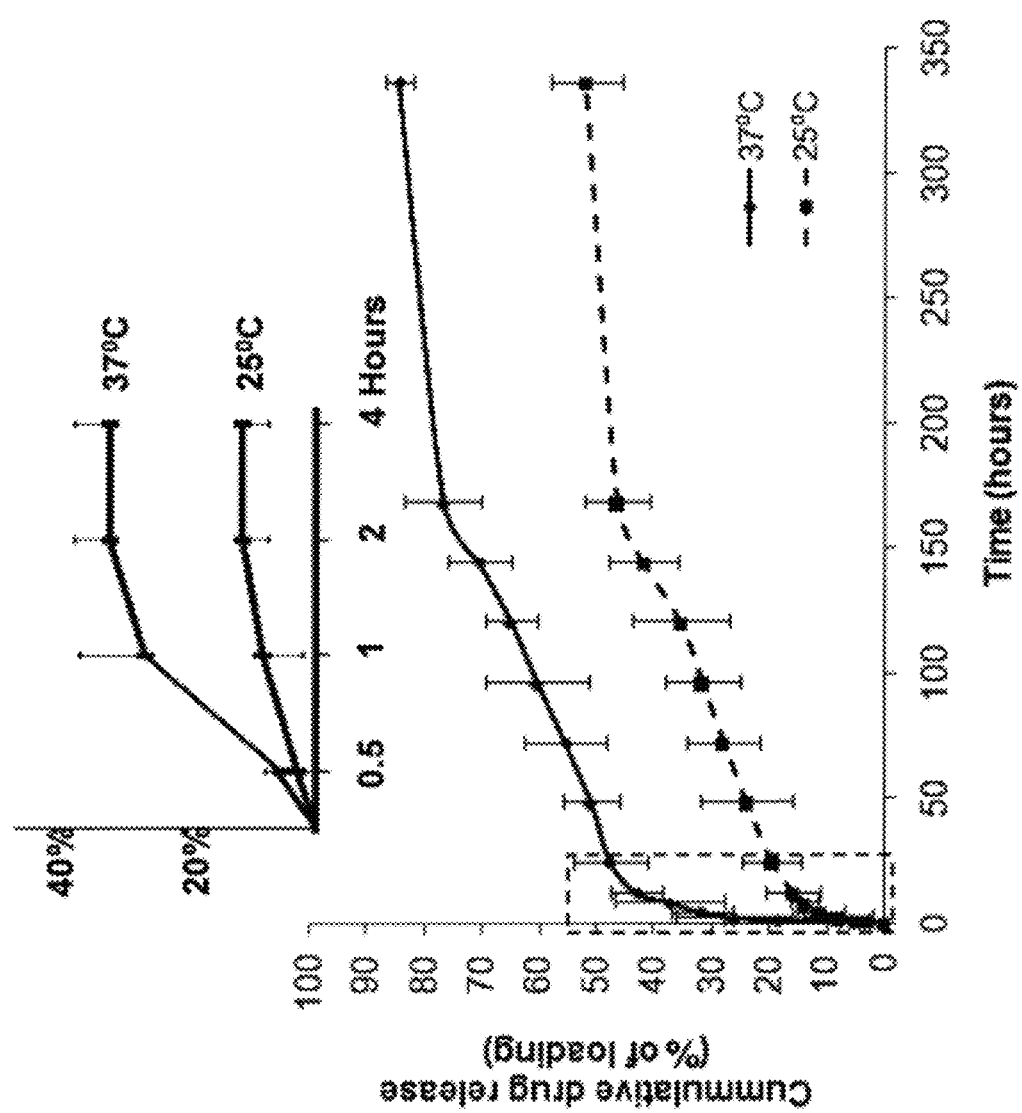

Nanoparticles with superparamagnetic behavior have attracted clinical attention for drug delivery for their unique property that they magnetize strongly in the presence of an external magnetic field but retain no permanent magnetism after the magnetic field is removed.[43,61] Thermo-responsive hydrogel based on pNIPA-AAm had been synthesized and functionalized for more than two decades.[61] At temperatures above the lower critical solution temperature (LCST), pNIPA-AAm hydrogel shrinks by expelling water molecules and releasing the payload molecules incorporated in the hydrogel. In Example 1, we successfully synthesized MNPs that had a LCST at 37° C. The release kinetic study showed that approximately 30% of the NIPA-M was released from the pNIPA-AAm hydrogel in the first two hours (FIG. 2B). Significant suppression of the targeted IRGP function was achieved 2 hours after intra-coronary infusion of the MNP. Although we were not capable of tracking the movement of individual MNPs and the in vivo release kinetics of the NIPA-M were not investigated, the sharp contrast of the effects on the ARGP and IRGP function indicated that the MNP were successfully targeted to the IRGP and sufficient NIPA-M was released within the IRGP to cause neurotoxicity and suppression of the IRGP function.

Neurotoxins such as botulinum toxin (i.e. BOTOX® a.k.a. BtA) have been used to treat various local diseases with minimal systemic side effects.[64,65] Monomers of acrylamide and its analogues including NIPA-M have a long history of producing systemic neurotoxicity in humans and experimental animals. Neuropathological studies suggested that acrylamide neurotoxicity was related to inhibition of glycolytic enzymes such as enolase, leading to toxic effects on both neurons and axons.[49,66,67] In the work described herein, the IRGP function was significantly suppressed by a single intra-coronary infusion which contains 0.8 mg of NIPA-M that was approximately 7 mM (0.8 mg in 1 ml, MW=113). The $LD_{50}$% of NIPA-M to kill 50% neurons was 5-8 mM.[68] Our histological evidence showed that epicardial fat and GP contained the greatest concentration of MNPs, suggesting that the concentration of NIPA-M in the GP would be much higher than the $LD_{50}$%. This may explain the findings that significant suppression of the GP function was observed in 2 hours after intra-coronary infusion of the MNPs. NIPA-M has also been reported to induce clinical (ataxia, rotorod performance deficits) and morphological (tibial nerve degeneration) signs of neuropathy following prolonged oral exposure (i.e. 2.65 mM in drinking water for 90 days or approximately 20 mg/kg/day).[49,68,69] Lower dosing rates (1-20 mg/kg/day) typically require 60 days to 2 years to elicit overt and morphological signs of neuropathy. 49,68,69 In Example 1, with an average body weight in dogs of 20-25 kg, this would result in a single exposure to NIPA-M of approximately 0.04 mg/kg. If NIPA-M was slowly released back into the circulation from the targeted GP, the concentration of the NIPA-M would be far below the threshold for inducing any systemic neurotoxicity. Moreover, Example 1 used a single application of the MNPs, to destroy the autonomic neurons concentrated in the GP, which do not regenerate, further lowering the risks associated with prolonged exposure to NIPA-M. Importantly, the results of Example 1 support a proffered embodiment of the presently disclosed and claimed inventive concepts, i.e., a magnetic targeted drug delivery for ablating the GP. Other agents contemplated herein may also be incorporated into the hydrogel matrix shell as the bioactive agent.

Example 1 demonstrates that intravascular-administered MNPs carrying a bioactive agent (e.g., NIPA-M) can be magnetically targeted to the IRGP and other GP and reduce GP activity by the subsequent release of NIPA-M toxin. This novel targeted drug delivery system can be used intravascularly for targeted autonomic denervation. With the advances in stereotactic localization of externally applied magnetic field, this novel approach will serve as a less invasive and less expensive therapeutic modality to treat drug-refractory AF.

Example 2

In another version of the presently disclosed and claimed inventive concepts, BtA was incorporated into MNP's and was used as the neurotoxicant payload. A permanent magnet (2600 gauss) was attached at the pole face over the inferior right GP (IRGP) of the heart in a dog. After the percent of maximal ventricular rate (VR) reduction induced by IRGP stimulation was documented, the core temperature of the dog was reduced from 37.5° C. to 35° C. BtA-MNPs carrying approximately 5 ng of BtA was infused into the circumflex coronary artery. The dog was kept at 35° C. for another hour to prevent premature release of BtA before the BtA-MNPs reached the targeted IRGP. Then, the core temperature was raised to 37.5° C.-37.8° C., above the lower critical solution temperature (LCST) (37° C.) at which the BtA payload was designed to be released from the polymer shell of the MNPs. Over the next 2 hours, there was a measurable decrease in the maximal VR reduction induced by the same IRGP stimulation indicating that BtA has a positive effect in inhibiting AF.

It will be understood that particular embodiments and examples described herein are shown by way of illustration and not as limitations of the presently disclosed and claimed inventive concepts. The principal features of the presently disclosed and claimed inventive concepts can be employed in various embodiments without departing from the scope thereof. Those skilled in the art will recognize, or be able to ascertain using no more than routine experimentation, numerous equivalents to the specific procedures described herein. Such equivalents are considered to be within the scope of the presently disclosed inventive concepts and are covered by the claims.

CITED REFERENCES

1. Benjamin E J, Wolf P A, D'Agostino R B et al. Impact of atrial fibrillation on the risk of death: The Framingham Heart Study. Circulation 1998; 98:946-952.
2. Caro J J. An economic model of stroke in atrial fibrillation: the cost of suboptimal oral anticoagulation. Am J Manag Care. 2004; 10(14 Suppl):S451-58; discussion S458-61.
3. Miyasaka Y, Barnes M E, Gersh B J, Cha S S, Bailey K R, Abhayaratna W P, Seward J B, Tsang T S. Secular trends in incidence of atrial fibrillation in Olmsted County, Minn., 1980 to 2000, and implications on the projections for future prevalence. Circulation. 2006 Jul. 11; 114:119-25.
4. Burton T M. Surgical device firms walk fine line. Wall Street Journal 2010; March 11; page A8.
5. Calkins H, Brugada J, Packer D L, Cappato R, Chen S A, Crijns H J, Damiano R J Jr, Davies D W, Haissaguerre M, Iesaka Y, Jackman W, Jais P, Kottkamp H, Kuck K H, Lindsay B D, Marchlinski F E, McCarthy P M, Mont J L, Morady F, Nademanee K, Natale A, Pappone C, Prystowsky E, Raviele A, Ruskin J N, Shemin R J. Heart Rhythm Society; European Heart Rhythm Association; European Cardiac Arrhythmia Society; American College of Cardiology; American Heart Association; Society of Thoracic Surgeons. HRS/EHRA/ECAS expert consensus statement on catheter and surgical ablation of atrial fibrillation: Recommendations for personnel.
6. Damiano R J. Surgical ablation of lone atrial fibrillation on the beating heart: the chaos continues. Europace. 2010 March; 12(3):297-8. Epub 2010 Feb. 5.
7. Shen J, Bailey M S, Damiano R J Jr. The surgical treatment of atrial fibrillation. Heart Rhythm. 2009 August; 6(8 Suppl):S45-50. Epub 2009 May 22.
8. Wilber D J, Pappone C, Neuzil P, De Paola A, Marchlinski F, Natale A, Macle L, Daoud E G, Calkins H, Hall B, Reddy V, Augello G, Reynolds M R, Vinekar C, Liu C Y, Berry S M, Berry D A; ThermoCool AF Trial Investigators. Comparison of antiarrhythmic drug therapy and radiofrequency catheter ablation in patients with paroxysmal atrial fibrillation: a randomized controlled trial. JAMA. 2010 Jan. 27; 303(4):333-40.
9. Bettoni M, Zimmermann. Autonomic tone variations before the onset of paroxysmal atrial fibrillation. *Circulation* 2002; 105:2753-2759.
10. Amar D, Zhang H, Miodownik S, Kadish A. Competing autonomic mechanisms precedes the onset of postoperative atirial fibrillation. *J Am Coll Cardio*. 2003; 42:1262-1268.
11. Ogawa M, Zhou S, Tan A Y, Song J, Gholmieh G, Fishbein M C, Lou H, Siegel R J, Karagueuzian H S, Chen L S, Lin S F, Chen P S. Left stellate ganglion and vagal nerve activity and cardiac arrhythmias in ambulatory dogs with pacing-induced congestive heart failure. *J Am Coll Cardiol*. 2007; 50:335-343.
12. Patterson E, Po S S, Scherlag B, Lazzara R. Triggered Firing in Pulmonary Veins Initiated by in vitro Autonomic Nerve Stimulation. Heart Rhythm 2005; 2:624-31.
13. Scherlag B J, Yamanashi W S, Patel U, Lazzara R, Jackman W M. Autonomically induced conversion of pulmonary vein focal firing into atrial fibrillation. J Am Coll Cardiol 2005; 45:1878-1886.
14. Po S S, Scherlag B J, Yamanashi W S, Edwards J, Zhou J, Wu R, Geng N, Lazzara R, Jackman W M. Experimental model for paroxysmal atrial fibrillation arising at the pulmonary vein-atrial junctions. Heart Rhythm. 2006; 3:201-208.
15. Randall W C, Armour J A, Geis W P, Lippincott D B. Regional cardiac distribution of the sympathetic nerves. Federation Proc. 1972; 31:1199-1208.
16. Ardell J L. Structure and Function of the Mammalian Intrinsic Cardiac Neurons. In: Neurocardiology. Eds: Armour J A, Ardell J L. Oxford University Press, New York, N.Y. 1994. Chap 5.
17. Pauza D H, Skripka V, Pauziene N. Morphology of the intrinsic cardiac nervous system in the dog: a whole-mount study employing histochemical staining with acetylcholinesterase. Cells Tissues Organs. 2002; 172(4):297-320.
18. Quan K J, Lee J H, Van Hare G F et al. Identification and characterization of atrioventricular parasympathetic innervation in humans. J Cardiovasc Electrophysiol 2002; 13:735-9.
19. Zhou J, Scherlag B J, Edwards J, Jackman W M, Lazzara R, Po S S. Gradients of atrial refractoriness and inducibility of atrial fibrillation due to stimulation of ganglionated plexi. J Cardiovasc Electrophysiol. 2007; 18:83-90.
20. Lu Z, Scherlag B J, Lin J, Niu G, Yu L, Jackman W M, Lazzara R, Jiang H, Po S S. Autonomic Mechanism for Initiation of Rapid Firing from Atria and Pulmonary Veins: Evidence by Ablation of Ganglionated Plexi. *Carviovas Res*. 2009; 84:245-52.
21. Lu Z, Scherlag B J, Lin J, Jackman W M, Lazzara R, Jiang H, Po S S. Atrial fibrillation begets atrial fibrillation: the role of autonomic nervous system in acute atrial remodeling. *Circulation* 2008; 1:184-192.
22. Pokushalov E, Romanov A, Shugayev P, Artyomenko S, Shirokova N, Turov A, Katritsis D G. Selective ganglionated plexi ablation for paroxysmal atrial fibrillation. Heart Rhythm 2009; 6:1257-1264.
23. Pokushalov E, Turov A, Shugayev P, Artyomenko S, Romanov A, Shirokova N, Catheter ablation of left atrial ganglionated plexi for atrial fibrillation. *Asian Cardiovasc Thorac Ann* 2008; 16:194-201.
24. Pokushalov E, Romanov A, Artyomenko S, Turov A, Shugayev P, Shirokova N, Katritsis D G. Ganglionated plexi ablation for longstanding persistent atrial fibrillation. Europace 2010; 12:342-346.
25. Sakamoto S, Schuessler R B, Lee A M, Aziz A, Lall S C, Damiano R J Jr. Vagal denervation and reinnervation after ablation of ganglionated plexi. J Thorac Cardiovasc Surg. 2010; 139(2):444-52.
26. Oh S, Zhang Y, Bibevski S, Marrouche N F, Natale A, Mazgalev T N. Vagal denervation and atrial fibrillation inducibility: epicardial fat pad ablation does not have long-term effects. Heart Rhythm. 2006 June; 3(6):701-8. Epub 2006 Mar. 6.
27. Bauer A, Deisenhofer I, Schneider R, Zrenner B, Barthel P, Karch M, Wagenpfeil S, Schmitt C, Schmidt G. Effects of circumferential or segmental pulmonary vein ablation for paroxysmal atrial fibrillation on cardiac autonomic function. Heart Rhythm. 2006; 3(12):1428-35.
28. Corot C, Robert P, Idee J M, Port M. Recent advances in iron oxide nanocrystal technology for medical imaging. Advanced Drug Delivery Reviews 2006; 58:1471-1504.
29. Ito A, Shinkai M, Honda H, Kobayshi T. Medical application of functionalized magnetic nanoparticles. Journal of Bioscience and Bioengineering 2005; 100:1-11.

30. Liapi E, Geschwind J F. Research and future directions in oncology embolotherapy, in. Golzarian E, Sun S, Sharafuddin M J. Vascular Embolotherapy, 2006: 221-232.
31. Kim J, Lee J E, Lee S H, Yu J H, Lee J H, Park T G, Hyeon T. Designed fabrication of a multifunctional polymer nanomedical platform from simultaneous cancer-targeted imaging and magnetically guided drug delivery. Advanced Materials 2008; 20:478-483.
32. Chen H, Gu Y, Hu Y, Qian Z. Characterization of pH- and temperature-sensitive hydrogel nanoparticles for controlled drug release. PDA J. Pharm. Sci. Tech. 2007(61): 303-313.
33. Prankhurst Q A, Connolly, J., Jones, S. K. et al. Applications to magnetic nanoparticles in biomedicine. *J. Phys. D. Applied Physics* 2003(36):R167-R81.
34. Gupta A K, Gupta M. Synthesis and surface engineering of iron oxide nanoparticles for biomedical applications. *Biomaterials* 2005(26):3995-4021.
35. Dormer K, Seeney C, Lewelling K et al. Epithelial internalization of superparamagnetic nanoparticles and response to external magnetic field. *Biomaterials* 2005 (26):2061-72.
36. Wakamatsu H, Yamamoto K, Nakao A, and Aoyagi T. Preparation and characterization of temperature-responsive nanoparticles conjugated with N-Isopropylacrilamide-based functional copolymer. J. Mag. Mag. Materials 2006(302):327-333.
37. Po S S, Nakagawa H, Jackman W M. Localization of Left Atrial Ganglionated Plexi in Patients with Atrial Fibrillation. J Cardiovasc Electrophysiol; 2009; 20:1186-9.
38. Scherlag B J, Nakagawa H, Jackman W M, Yamanashi S W, Patterson E, Po S, Lazzara R. Electrical stimulation to identify neural elements on the heart: Their role in atrial fibrillation. J Interv Card Electrophysiol. 2005; 13:37-42.
39. Danik S, Neuzil P, Avila A, Malchano Z J, Kralovec S, Ruskin J N, Reddy V Y. Evaluation of catheter ablation of periatrial ganglionic plexi in patients with atrial fibrillation. Am J Cardiol. 2008; 102:578-583.
40. Pokushalov E, Romanov A, Shugayev P, Artyomenko S, Shirokova N, Turov A, Katritsis D G. Selective ganglionated plexi ablation for paroxysmal atrial fibrillation. Heart Rhythm. 2009; 6:1257-64.
41. Pokushalov E, Turov A, Shugayev P, Artyomenko S, Romanov A, Shirokova N. Catheter ablation of left atrial ganglionated plexi for atrial fibrillation. Asian Cardiovasc Thorac Ann. 2008; 16:194-201.
42. Pokushalov E. The role of autonomic denervation during catheter ablation of atrial fibrillation. Curr Opin Cardiol. 2008; 23:55-9.
43. Neuberger T, Schöpf B, Hofmann H, Hofmann M, Rechenberg B V. Superparamagnetic nanoparticles for biomedical applications: Possibilities and limitations of a new drug delivery system. J Magn Magn Mater. 2005; 293:483-96.
44. Corot C, Robert P, Idee J M, Port M. Recent advances in iron oxide nanocrystal technology for medical imaging. Adv Drug Deliv Rev. 2006; 58:1471-504.
45. Ito A, Shinkai M, Honda H, Kobayshi T. Medical application of functionalized magnetic nanoparticles. J Biosci Bioeng. 2005; 100:1-11.
46. Kim J, Lee J E, Lee S H, Yu J H, Lee J H, Park T G, Hyeon T. Designed fabrication of a multifunctional polymer nanomedical platform from simultaneous cancer-targeted imaging and magnetically guided drug delivery. Adv Mater. 2008; 20:478-83.
47. Dormer K, Seeney C, Lewelling K, Lian G, Gibson D, Johnson M. Epithelial internalization of superparamagnetic nanoparticles and response to external magnetic field. Biomaterials. 2005; 26:2061-2072.
48. Lu Z, Scherlag B J, Lin J, Niu G, Fung K M, Zhao L, Ghias M, Jackman W M, Lazzara R, Jiang H, Po S S. Atrial fibrillation begets atrial fibrillation: autonomic mechanism for atrial electrical remodeling induced by short-term rapid atrial pacing. Circ Arrhythm Electrophysiol. 2008; 1:184-92.
49. LoPachin R M. Acrylamide neurotoxicity: neurological, morhological and molecular endpoints in animal models. Adv Exp Med Biol. 2005; 561:21-37.
50. Scherlag B J, Yamanashi W S, Patel U, Lazzara R, Jackman W M. Autonomically induced conversion of pulmonary vein focal firing into atrial fibrillation. J Am Coll Cardiol. 2005; 45:1878-1886.
51. Gupta A K, Gupta M. Synthesis and surface engineering of iron oxide nanoparticles for biomedical applications. Biomaterials. 2005; 26:3995-4021.
52. Rahimi M, Youself M, Cheng Y, Meletis El, Eberhart R C, Nguyen K T. Formulation and characterization of covalently coated magnetic nanogel. J Nanosci Nanotechnol 2009; 9:4128-4134.
53. Wakamatsu H, Yamamoto K, Nakao A, and Aoyagi T. Preparation and characterization of temperature-responsive nanoparticles conjugated with N-Isopropylacrilamide-based functional copolymer. J Magn Magn Mater. 2006; 302:327-333.
54. Wadajkar A, Koppolu B, Rahimi M, Nguyen K T. Cytotoxic evaluation of N-isopropylacrylamide monomers and temperature-sensitive poly(N-isopropylacrylamide) nanoparticles. J Nanopart Res. 2009; 11:1375-1382.
55. Rahimi M, Kilaru S, El Hajj Sleiman G, Saleh A, Rudkevich D, Nguyen K T. Synthesis and characterization of thermo-sensitive nanoparticles for drug delivery applications. J. Biomed. Nanotechnol. 2008; 4:482-90.
56. Chastek T, Wadajkar A, Nguyen K T, Hudson S D, Chastek T. Polyglycol-templated Synthesis of Poly(N-Isopropyl Acrylamide) Microgels with Improved Biocompatibility. Colloid Polym Sci. 2010; 288:105-114.
57. Zhou J, Scherlag B J, Edwards J, Jackman W M, Lazzara R, Po S S. Gradients of atrial refractoriness and inducibility of atrial fibrillation due to stimulation of ganglionated plexi. J Cardiovasc Electrophysiol. 2007; 18:83-90.
58. Hou Y, Scherlag B J, Lin J, Lu Z, Truong K, Patterson E, Lazzara R, Jackman W, Po S S. Ganglionated plexi modulating extrinsic cardiac autonomic nervous inputs: Effects on sinus rate, AV conduction, refractoriness and AF inducibility. J Am Coll Cardiol. 2007; 50:61-68.
59. Hou Y, Scherlag B J, Zhou J, Song J, Patterson E, Lazzara R, Jackman W M, Po S S. Interactive Atrial Neural Network: Determining the Connections between Ganglionated Plexi. Heart Rhythm. 2007; 4:56-63.
60. Po S S, Scherlag B J, Yamanashi W S, Edwards J, Zhou J, Wu R, Geng N, Lazzara R, Jackman W M. Experimental model for paroxysmal atrial fibrillation arising at the pulmonary vein-atrial junctions. Heart Rhythm. 2006; 3:201-208.
61. Pelton R. Temperature-sensitive aqueous microgels. Adv Colloid Interface Sci. 2000; 85:1-33.
62. Lin J, Scherlag B J, Zhou J, Lu Z, Patterson E, Jackman W M, Lazzara R, Po S S. Autonomic Mechanism to Explain Complex Fractionated Atrial Electrograms (CFAE). J Cardiovasc Electrophysiol. 2007; 18:1197-205.
63. Niu G, Scherlag B J, Lu Z, Ghias M, Zhang Y, Patterson E, Dasari T W, Zacharias S, Lazzara R, Jackman W M, Po S S. An acute experimental model demonstrating 2 different forms of sustained atrial tachyarrhythmias. Circ Arrhythm Electrophysiol. 2009; 2:384-92.
64. Brashear A. The safety and tolerability of botulinum toxin for the treatment of cervical dystonia. Expert Opin Drug Saf. 2005; 4:241-249.
65. Brin M F. Development of future indications for BOTOX®. Toxicon. 2009; 54:668-74.

66. Tanil H, Hashimoto K. Effect of acrylamide and related compounds on glycolytic enzymes of rat brain. Toxicol Lett. 1985; 26:79-84.
67. Howland R D. The etiology of acrylamide neuropathy: enolase, phosphofructokinase and glyceraldehyde-3-phosphotase dehydrogenase activities in peripheral nerve, spinal cord, brain and skeletal muscle of acrylamide-intoxicated cats. Toxicol Appl Pharmacol. 1981; 60:324-33.
68. LoPachin R M, Ross J F, Reid M L, Das S, Mansukhani S, Lehning E J. Neurological evaluation of toxic axonopathies in rats: acrylamide and 2,5-hexanedione. Neurotoxicology. 2002; 23: 95-110.
69. Lopachin R M, Gavin T. Acrylamide-induced nerve terminal damage: relevance to neurotoxic and neurodegenerative mechanisms. J Agric Food Chem. 2008; 56: 5994-6003.
70. Benjamin E J, Wolf P A, D'Agostino R B, Silbershatz H, Kannel W B, Levy D. Impact of atrial fibrillation on the risk of death: The Framingham Heart Study. Circulation. 1998; 98:946-52.

All patents, published patent applications, articles, references, or other publications cited anywhere herein are explicitly incorporated herein by reference in their entireties.

What is claimed is:

1. A method of treating a cardiac disorder in a subject in need of such treatment, comprising:
    administering a nanoparticle composition to a vascular component of the subject, the nanoparticle composition comprising a plurality of nanoparticles, each nanoparticle comprising a magnetically-susceptible core, a biocompatible polymer shell which surrounds the magnetically-susceptible core, and an active agent which is embedded, loaded, and/or absorbed on or within, or otherwise linked, attached, and/or bound to the biocompatible polymer shell;
    establishing a magnetic gradient about a targeted portion of the intrinsic cardiac autonomic nervous system (intrinsic CANS) of the subject, the targeted portion comprising at least one ganglionated plexi, the magnetic gradient causing the nanoparticles to be retained in the targeted portion of the intrinsic CANS, and wherein the active agent is released from the biocompatible polymer shell of the nanoparticles causing reduction or suppression of the at least one ganglionated plexi, thereby treating the cardiac disorder.

2. The method of claim 1 wherein the magnetically-susceptible core of the nanoparticle comprises a superparamagnetic material.

3. The method of claim 2 wherein the superparamagnetic material comprises magnetite, maghemite, hematite, FeNi, FePt, Fe, or FeCoNi alloy.

4. The method of claim 1 wherein the nanoparticles have a major diameter in a range of 2-500 nm.

5. The method of claim 4 wherein the nanoparticles have a major diameter in a range of 10-200 nm.

6. The method of claim 1 wherein the active agent comprises one or more of botulinum toxin, N-isopropylacrylamide monomer, botulinum toxin-alpha, hemicholinium-3, 192-IgG-toxin, or 6-hydroxydopamine.

7. The method of claim 1 wherein the active agent comprises botulinum toxin.

8. The method of claim 1 wherein the biocompatible polymer shell is biodegradable.

9. The method of claim 1 wherein the magnetic gradient is established about the targeted portion of the intrinsic CANS via an electromagnet which is external to the chest cavity of the subject.

10. The method of claim 1 wherein the at least one ganglionated plexi is selected from the anterior right ganglionated plexi, the inferior right ganglionated plexi, the superior left ganglionated plexi, the inferior left ganglionated plexi, and the ligament of Marshall.

11. The method of claim 1 wherein the targeted portion of the intrinsic CANS further comprises the PV-atrial junction.

12. The method of claim 1 wherein the cardiac disorder is an atrial disorder.

13. The method of claim 12 wherein the cardiac disorder is an atrial fibrillation.

14. The method of claim 1 wherein the cardiac disorder is a ventricular disorder.

15. The method of claim 1 wherein the reduction or suppression of the at least one ganglionated plexi of the cardiac autonomic nervous system is temporary.

16. The method of claim 1 wherein the active agent comprises a neurotoxin.

17. The method of claim 1 wherein the biocompatible polymer shell is thermo-labile, wherein the biocompatible polymer shell is induced to release the active agent upon reaching a temperature of about 37° C. or greater.

18. The method of claim 1 wherein the active agent of the nanoparticles is permanently-acting.

19. A method of treating an atrial fibrillation in a subject in need of such treatment, comprising:
    administering a nanoparticle composition to a vascular component of the subject, the nanoparticle composition comprising a plurality of nanoparticles, each nanoparticle comprising a magnetite core, a biocompatible polymer shell which surrounds the magnetite core, and a botulinum toxin on or within the biocompatible polymer shell;
    establishing a magnetic gradient about at least one ganglionated plexi of the heart causing the nanoparticles to be retained in the at least one ganglionated plexi of the heart, and wherein the botulinum toxin is released from the biocompatible polymer shell of nanoparticles for treatment of or application to the at least one ganglionated plexi of the heart causing reduction or suppression of the at least one ganglionated plexi of the heart, thereby treating the atrial fibrillation.

20. The method of claim 19 wherein the nanoparticles have a major diameter in a range of 2-500 nm.

21. The method of claim 20 wherein the nanoparticles have a major diameter in a range of 10-200 nm.

22. The method of claim 19 wherein the biocompatible polymer shell is bio-degradable.

23. The method of claim 19 wherein the magnetic gradient is established about the at least one ganglionated plexi of the heart via an electromagnet which is external to the chest cavity of the subject.

24. The method of claim 19 wherein the at least one ganglionated plexi is selected from the anterior right ganglionated plexi, the inferior right ganglionated plexi, the superior left ganglionated plexi, the inferior left ganglionated plexi, and the ligament of Marshall.

25. The method of claim 19 wherein the biocompatible polymer shell is thermo-labile, wherein the biocompatible polymer shell is induced to release the botulinum toxin upon reaching a temperature of about 37° C. or greater.

* * * * *

UNITED STATES PATENT AND TRADEMARK OFFICE
CERTIFICATE OF CORRECTION

PATENT NO. : 8,740,872 B2  
APPLICATION NO. : 12/907806  
DATED : June 3, 2014  
INVENTOR(S) : Kenneth J. Dormer et al.

Page 1 of 1

It is certified that error appears in the above-identified patent and that said Letters Patent is hereby corrected as shown below:

In the Specification:

Column 1, line 42: Delete "litigations.$^{4}$" and replace with -- litigations.$^{4}$ --

Column 6, line 27: Delete "$^{45,49}$" and replace with -- $^{48,49}$ --

In the Claims:

Column 23, line 35: After "shell;" insert -- and --

Signed and Sealed this  
Fifth Day of August, 2014

Michelle K. Lee  
*Deputy Director of the United States Patent and Trademark Office*